US009179831B2

(12) United States Patent
McGrail et al.

(10) Patent No.: US 9,179,831 B2
(45) Date of Patent: Nov. 10, 2015

(54) VISUALIZATION INSTRUMENT

(75) Inventors: Thomas W. McGrail, Cicero, IN (US);
Michael S. Pargett, West Lafayette, IN (US); David J. Miller, Noblesville, IN (US); Yun Siung Tony Yeh, Libertyville, IL (US); Randal B. Chinnock, Eastford, CT (US); George Grubner, Needham, MA (US); Elizabeth Powell Goodrich, Roslidale, MA (US); Richard L. Miller, Needham, MA (US); Gary Vincent Palladino, Cambridge, MA (US); Brian Hack, Cambridge, MA (US)

(73) Assignee: King Systems Corporation, Noblesville, IN (US)

( * ) Notice: Subject to any disclaimer, the term of this patent is extended or adjusted under 35 U.S.C. 154(b) by 314 days.

(21) Appl. No.: 12/874,035

(22) Filed: Sep. 1, 2010

(65) Prior Publication Data
US 2011/0130632 A1    Jun. 2, 2011

Related U.S. Application Data

(60) Provisional application No. 61/314,058, filed on Mar. 15, 2010, provisional application No. 61/265,330, filed on Nov. 30, 2009.

(51) Int. Cl.
*A61B 1/267* (2006.01)
*A61B 1/00* (2006.01)
*A61B 1/05* (2006.01)
(Continued)

(52) U.S. Cl.
CPC ............. *A61B 1/267* (2013.01); *A61B 1/00016* (2013.01); *A61B 1/00052* (2013.01); *A61B 1/00103* (2013.01); *A61B 1/00105* (2013.01); *A61B 1/05* (2013.01); *G02B 23/2423* (2013.01); *G02B 23/2446* (2013.01); *A61B 1/018* (2013.01)

(58) Field of Classification Search
USPC .................. 600/187, 188, 190, 194, 120, 122
See application file for complete search history.

(56) References Cited

U.S. PATENT DOCUMENTS

| 3,766,909 A | 10/1973 | Ozbey |
| 3,771,514 A | 11/1973 | Huffman et al. |
| 4,114,609 A | 9/1978 | Moses |

(Continued)

FOREIGN PATENT DOCUMENTS

| EP | 1640033 | 3/2006 |
| EP | 1977685 | 10/2008 |

(Continued)

OTHER PUBLICATIONS

Coopdech VLP-100 Video Laryngoscope advertising in fero-medic.com web page; last accessed on Aug. 31, 2010 at http://www.fero-medic.com; 1 page.

(Continued)

*Primary Examiner* — Nicholas Woodall
*Assistant Examiner* — Olivia C Chang
(74) *Attorney, Agent, or Firm* — Faegre Baker Daniels LLP

(57) ABSTRACT

A visualization instrument comprising a display support component removably coupled to a component insertable into a target space. The insertable component includes a camera providing images of the target space. The images are presented in a display device supported by the display support component. The insertable component may be discarded after a permitted number of uses.

27 Claims, 30 Drawing Sheets

(51) Int. Cl.
*G02B 23/24* (2006.01)
*A61B 1/018* (2006.01)

(56) References Cited

U.S. PATENT DOCUMENTS

| | | | |
|---|---|---|---|
| 4,126,127 A | 11/1978 | May | |
| 4,360,008 A | 11/1982 | Corazzelli, Jr. | |
| 4,573,451 A | 3/1986 | Bauman | |
| 4,592,343 A | 6/1986 | Upsher | |
| 4,611,579 A | 9/1986 | Bellhouse | |
| 4,742,819 A | 5/1988 | George | |
| 4,793,327 A | 12/1988 | Frankel | |
| 4,832,004 A | 5/1989 | Heckele | |
| 4,846,153 A | 7/1989 | Berci | |
| 4,947,896 A | 8/1990 | Bartlett | |
| 4,982,729 A | 1/1991 | Wu | |
| 5,003,962 A | 4/1991 | Choi | |
| 5,016,614 A | 5/1991 | MacAllister | |
| 5,038,766 A | 8/1991 | Parker | |
| 5,042,469 A | 8/1991 | Augustine | |
| 5,095,888 A | 3/1992 | Hawley | |
| 5,183,031 A | 2/1993 | Rossoff | |
| 5,202,795 A | 4/1993 | Kashima | |
| 5,203,320 A | 4/1993 | Augustine | |
| 5,261,392 A | 11/1993 | Wu | |
| 5,287,848 A | 2/1994 | Cubb et al. | |
| 5,329,940 A | 7/1994 | Adair | |
| 5,339,805 A | 8/1994 | Parker | |
| 5,363,838 A | 11/1994 | George | |
| 5,381,787 A | 1/1995 | Bullard | |
| 5,400,771 A | 3/1995 | Pirak et al. | |
| 5,431,152 A | 7/1995 | Flam et al. | |
| 5,443,058 A | 8/1995 | Ough | |
| 5,489,256 A | 2/1996 | Adair | |
| 5,498,231 A | 3/1996 | Franicevic | |
| 5,513,627 A | 5/1996 | Flam | |
| 5,551,946 A | 9/1996 | Bullard | |
| 5,603,688 A | 2/1997 | Upsher | |
| 5,643,175 A | 7/1997 | Adair | |
| 5,645,519 A | 7/1997 | Lee et al. | |
| 5,665,052 A | 9/1997 | Bullard | |
| 5,676,635 A | 10/1997 | Levin | |
| 5,716,323 A | 2/1998 | Lee | |
| 5,776,052 A | 7/1998 | Callahan | |
| 5,800,344 A | 9/1998 | Wood, Sr. et al. | |
| 5,803,898 A | 9/1998 | Bashour | |
| 5,819,733 A | 10/1998 | Bertram | |
| 5,827,178 A | 10/1998 | Berall | |
| 5,842,973 A | 12/1998 | Bullard | |
| 5,845,634 A | 12/1998 | Parker | |
| 5,873,814 A | 2/1999 | Adair | |
| 5,879,289 A | 3/1999 | Yarush et al. | |
| 5,913,817 A | 6/1999 | Lee | |
| 5,929,901 A | 7/1999 | Adair et al. | |
| 5,986,693 A | 11/1999 | Adair et al. | |
| 6,043,839 A | 3/2000 | Adair et al. | |
| 6,046,769 A | 4/2000 | Ikeda et al. | |
| 6,079,409 A | 6/2000 | Brain | |
| 6,097,423 A | 8/2000 | Mattsson-Boze et al. | |
| 6,099,465 A | 8/2000 | Inoue | |
| 6,115,523 A | 9/2000 | Choi et al. | |
| 6,142,144 A | 11/2000 | Pacey | |
| 6,174,281 B1 | 1/2001 | Abramowitz | |
| 6,190,308 B1 | 2/2001 | Irion et al. | |
| 6,248,061 B1 | 6/2001 | Cook, Jr. | |
| 6,275,255 B1 | 8/2001 | Adair et al. | |
| 6,310,642 B1 | 10/2001 | Adair et al. | |
| 6,322,498 B1 | 11/2001 | Gravenstein et al. | |
| 6,354,993 B1 | 3/2002 | Kaplan et al. | |
| 6,396,873 B1 | 5/2002 | Goldstein et al. | |
| 6,413,209 B1 | 7/2002 | Thompson | |
| 6,432,042 B1 | 8/2002 | Bashour | |
| 6,432,046 B1 | 8/2002 | Yarush et al. | |
| 6,449,007 B1 | 9/2002 | Yokoyama | |
| 6,494,826 B1 | 12/2002 | Chatenever et al. | |
| 6,494,828 B1 | 12/2002 | Berall | |
| 6,623,425 B2 | 9/2003 | Cartledge et al. | |
| 6,652,453 B2 | 11/2003 | Smith et al. | |
| 6,655,377 B2 | 12/2003 | Pacey | |
| 6,656,110 B1 | 12/2003 | Irion et al. | |
| 6,663,560 B2 | 12/2003 | Macaulay | |
| 6,676,598 B2 | 1/2004 | Rudischhauser | |
| 6,750,037 B2 | 6/2004 | Adair et al. | |
| 6,753,160 B2 | 6/2004 | Adair et al. | |
| 6,792,948 B2 | 9/2004 | Brain | |
| 6,830,049 B2 | 12/2004 | Augustine et al. | |
| 6,832,986 B2 | 12/2004 | Chibber et al. | |
| 6,840,903 B2 | 1/2005 | Mazzei et al. | |
| 6,843,769 B1 | 1/2005 | Gandarias | |
| 6,870,566 B1 | 3/2005 | Koide et al. | |
| 6,875,169 B2 | 4/2005 | Berci et al. | |
| 6,890,298 B2 | 5/2005 | Berci et al. | |
| 6,901,928 B2 | 6/2005 | Loubser | |
| 6,923,663 B2 | 8/2005 | Oddsen et al. | |
| 6,929,600 B2 | 8/2005 | Hill | |
| 6,982,740 B2 | 1/2006 | Adair | |
| 6,982,742 B2 | 1/2006 | Adair | |
| 6,984,205 B2 | 1/2006 | Gazdzinski | |
| 7,030,904 B2 | 4/2006 | Adair et al. | |
| 7,044,910 B2 | 5/2006 | Cartledge et al. | |
| 7,048,686 B2 | 5/2006 | Kameya et al. | |
| 7,110,808 B2 | 9/2006 | Adair | |
| 7,116,352 B2 | 10/2006 | Yaron | |
| 7,128,071 B2 | 10/2006 | Brain | |
| 7,134,992 B2 | 11/2006 | Schara et al. | |
| 7,154,527 B1 | 12/2006 | Goldstein et al. | |
| D534,652 S | 1/2007 | McGrath | |
| 7,156,091 B2 | 1/2007 | Koyama et al. | |
| 7,159,589 B2 | 1/2007 | Brain | |
| 7,182,728 B2 | 2/2007 | Cubb et al. | |
| 7,212,227 B2 | 5/2007 | Amling et al. | |
| 7,243,653 B2 | 7/2007 | Nelson | |
| 7,289,139 B2 | 10/2007 | Amling et al. | |
| 7,297,105 B2 | 11/2007 | Mackin | |
| 7,305,985 B2 | 12/2007 | Brain | |
| 7,369,176 B2 | 5/2008 | Sonnenschein | |
| 7,383,599 B2 | 6/2008 | Gabbay | |
| 7,448,377 B2 | 11/2008 | Koyama et al. | |
| 7,471,310 B2 | 12/2008 | Amling et al. | |
| 7,480,402 B2 | 1/2009 | Bar/Zohar et al. | |
| 7,485,375 B2 | 2/2009 | Tokuda et al. | |
| 7,493,901 B2 | 2/2009 | Brain | |
| 7,511,732 B2 | 3/2009 | Ellison et al. | |
| 7,563,227 B2 | 7/2009 | Gardner | |
| 7,658,708 B2 | 2/2010 | Schwartz et al. | |
| 7,683,926 B2 | 3/2010 | Schechterman et al. | |
| 7,771,350 B2 | 8/2010 | Geist et al. | |
| 7,909,757 B2 | 3/2011 | Herman | |
| 7,909,759 B2 | 3/2011 | Pecherer | |
| 7,946,981 B1 * | 5/2011 | Cubb | 600/194 |
| 2001/0004768 A1 | 6/2001 | Hodge et al. | |
| 2001/0013345 A1 | 8/2001 | Bertram | |
| 2001/0014768 A1 | 8/2001 | Kaplan et al. | |
| 2001/0033326 A1 | 10/2001 | Goldstein | |
| 2001/0054425 A1 | 12/2001 | Bertram | |
| 2002/0010417 A1 | 1/2002 | Bertram | |
| 2002/0022769 A1 | 2/2002 | Smith | |
| 2002/0103494 A1 | 8/2002 | Pacey | |
| 2003/0195390 A1 | 10/2003 | Graumann | |
| 2004/0019256 A1 | 1/2004 | Cubb | |
| 2004/0028390 A9 | 2/2004 | Chatenever et al. | |
| 2004/0122292 A1 | 6/2004 | Dey | |
| 2004/0127770 A1 | 7/2004 | McGrath | |
| 2004/0133072 A1 | 7/2004 | Kennedy | |
| 2004/0215061 A1 | 10/2004 | Kimmel et al. | |
| 2005/0059863 A1 | 3/2005 | Zilch | |
| 2005/0080342 A1 | 4/2005 | Gilreath et al. | |
| 2005/0090712 A1 | 4/2005 | Cubb | |
| 2005/0090715 A1 | 4/2005 | Schorer | |
| 2005/0159649 A1 | 7/2005 | Patel | |
| 2005/0182297 A1 | 8/2005 | Gravenstein et al. | |
| 2005/0187434 A1 | 8/2005 | Dey et al. | |
| 2005/0192481 A1 | 9/2005 | Berci et al. | |
| 2005/0240081 A1 | 10/2005 | Eliachar | |

(56) References Cited

U.S. PATENT DOCUMENTS

| | | |
|---|---|---|
| 2005/0244801 A1 | 11/2005 | DeSalvo |
| 2005/0279355 A1 | 12/2005 | Loubser |
| 2006/0004258 A1 | 1/2006 | Sun et al. |
| 2006/0004260 A1 | 1/2006 | Boedeker et al. |
| 2006/0015008 A1 | 1/2006 | Kennedy |
| 2006/0020166 A1 | 1/2006 | Berall |
| 2006/0020171 A1 | 1/2006 | Gilreath |
| 2006/0022234 A1 | 2/2006 | Adair et al. |
| 2006/0050144 A1 | 3/2006 | Kennedy |
| 2006/0079734 A1 | 4/2006 | Miyagi |
| 2006/0119621 A1 | 6/2006 | Krier |
| 2006/0162730 A1 | 7/2006 | Glassenberg et al. |
| 2006/0180155 A1 | 8/2006 | Glassenberg et al. |
| 2006/0241476 A1 | 10/2006 | Loubser |
| 2006/0276693 A1 | 12/2006 | Pacey |
| 2006/0276694 A1 | 12/2006 | Gandarias |
| 2007/0024717 A1 | 2/2007 | Chatenever et al. |
| 2007/0030345 A1 | 2/2007 | Amling et al. |
| 2007/0049794 A1 | 3/2007 | Glassenberg et al. |
| 2007/0068530 A1 | 3/2007 | Pacey |
| 2007/0074728 A1 | 4/2007 | Rea |
| 2007/0093693 A1 | 4/2007 | Geist et al. |
| 2007/0095352 A1 | 5/2007 | Berall |
| 2007/0106117 A1 | 5/2007 | Yokota |
| 2007/0106121 A1 | 5/2007 | Yokota |
| 2007/0106122 A1 | 5/2007 | Yokota et al. |
| 2007/0129603 A1 | 6/2007 | Hirsh |
| 2007/0137651 A1 | 6/2007 | Glassenberg et al. |
| 2007/0139953 A1 | 6/2007 | Krattiger et al. |
| 2007/0156022 A1 | 7/2007 | Patel |
| 2007/0162095 A1 | 7/2007 | Kimmel et al. |
| 2007/0167686 A1 | 7/2007 | McGrath |
| 2007/0173697 A1 | 7/2007 | Dutcher et al. |
| 2007/0175482 A1 | 8/2007 | Kimmel et al. |
| 2007/0179342 A1 | 8/2007 | Miller |
| 2007/0182842 A1 | 8/2007 | Sonnenschein et al. |
| 2007/0195539 A1 | 8/2007 | Birnkrant |
| 2007/0197873 A1 | 8/2007 | Birnkrant |
| 2007/0215162 A1 | 9/2007 | Glassenberg et al. |
| 2007/0265492 A1 | 11/2007 | Sonnenschein et al. |
| 2007/0265498 A1 | 11/2007 | Ito |
| 2007/0276436 A1 | 11/2007 | Sonnenschein et al. |
| 2007/0299313 A1 | 12/2007 | McGrath |
| 2008/0004498 A1 | 1/2008 | Pecherer |
| 2008/0009674 A1 | 1/2008 | Yaron |
| 2008/0029100 A1 | 2/2008 | Glassenberg et al. |
| 2008/0045801 A1 | 2/2008 | Shalman et al. |
| 2008/0051628 A1 | 2/2008 | Pecherer |
| 2008/0055400 A1 | 3/2008 | Schechterman et al. |
| 2008/0064926 A1 | 3/2008 | Chen |
| 2008/0091064 A1 | 4/2008 | Laser |
| 2008/0097161 A1 | 4/2008 | Wang et al. |
| 2008/0158343 A1 | 7/2008 | Schechterman et al. |
| 2008/0158344 A1 | 7/2008 | Schechterman et al. |
| 2008/0177146 A1 | 7/2008 | Chen |
| 2008/0177148 A1 | 7/2008 | Chen et al. |
| 2008/0200761 A1 | 8/2008 | Schwartz et al. |
| 2008/0211634 A1 | 9/2008 | Hopkins et al. |
| 2008/0236575 A1 | 10/2008 | Chuda |
| 2008/0249355 A1 | 10/2008 | Birnkrant |
| 2008/0249370 A1 | 10/2008 | Birnkrant et al. |
| 2008/0294010 A1 | 11/2008 | Cooper |
| 2008/0300475 A1 | 12/2008 | Jaeger et al. |
| 2008/0312507 A1 | 12/2008 | Kim |
| 2009/0022393 A1 | 1/2009 | Bar/Zohar et al. |
| 2009/0032016 A1 | 2/2009 | Law et al. |
| 2009/0065000 A1 | 3/2009 | Chen |
| 2009/0114217 A1 | 5/2009 | Wulfsohn et al. |
| 2009/0118580 A1 | 5/2009 | Sun et al. |
| 2009/0123135 A1 | 5/2009 | Amling et al. |
| 2009/0143645 A1 | 6/2009 | Matthes |
| 2009/0179985 A1 | 7/2009 | Amling |
| 2009/0187078 A1 | 7/2009 | Dunlop |
| 2009/0192350 A1 | 7/2009 | Mejia |
| 2009/0198111 A1 | 8/2009 | Nearman |
| 2009/0209826 A1 | 8/2009 | Sanders et al. |
| 2009/0235935 A1 | 9/2009 | Pacey |
| 2009/0247833 A1 | 10/2009 | Tanaka |
| 2009/0253955 A1 | 10/2009 | Akiba |
| 2009/0264708 A1 | 10/2009 | Pacey et al. |
| 2009/0287059 A1 | 11/2009 | Patel |
| 2009/0299146 A1 | 12/2009 | McGrath |
| 2009/0318758 A1 | 12/2009 | Farr et al. |
| 2009/0318768 A1 | 12/2009 | Tenger et al. |
| 2009/0318769 A1 | 12/2009 | Tenger et al. |
| 2009/0322867 A1 | 12/2009 | Carrey et al. |
| 2010/0022829 A1 | 1/2010 | Irion et al. |
| 2010/0022843 A1 | 1/2010 | Pecherer et al. |
| 2010/0069722 A1 | 3/2010 | Shalman et al. |
| 2010/0087708 A1 | 4/2010 | Chen et al. |
| 2010/0094090 A1 | 4/2010 | Mejia |
| 2010/0101569 A1 | 4/2010 | Kim et al. |
| 2010/0121152 A1 | 5/2010 | Boedeker |
| 2010/0141744 A1 | 6/2010 | Amling et al. |
| 2010/0152541 A1 | 6/2010 | Tenger et al. |
| 2010/0168521 A1 | 7/2010 | Gandarias |
| 2010/0191054 A1 | 7/2010 | Supiez |
| 2010/0191061 A1 | 7/2010 | Simons |
| 2010/0192355 A1 | 8/2010 | Zhao et al. |
| 2010/0198009 A1 | 8/2010 | Farr et al. |
| 2010/0224187 A1 | 9/2010 | Dalton |
| 2010/0249513 A1 | 9/2010 | Tydlaska |
| 2010/0249639 A1 | 9/2010 | Bhatt |
| 2010/0256451 A1 | 10/2010 | McGrath et al. |
| 2010/0261967 A1 | 10/2010 | Pacey et al. |
| 2010/0261968 A1 | 10/2010 | Nearman et al. |
| 2010/0288272 A1 | 11/2010 | Yokota et al. |

FOREIGN PATENT DOCUMENTS

| | | |
|---|---|---|
| WO | WO 2006/102770 | 10/2006 |
| WO | WO 2008/019367 | 2/2008 |
| WO | WO 2009/130666 | 10/2009 |
| WO | WO 2010/049694 | 5/2010 |
| WO | WO 2010/066787 | 6/2010 |
| WO | WO 2010/066790 | 6/2010 |
| WO | WO 2010/100496 | 9/2010 |
| WO | WO 2010/100498 | 9/2010 |

OTHER PUBLICATIONS

GlideScope® Ranger advertising web page; last accessed on Aug. 31, 2010 at http://www.verathon.com/gs_ranger.htm; 2 pages.

McGrath® Video Laryngoscope Series 5 advertising web page; last accessed on Aug. 31, 2010 at http://www.medtel.com.au; 2 pages.

Res-Q-Tech Res-Q-Scope® II advertising web page; last accessed Oct. 13, 2009 at http://www.res-q-tech-na.com/products.html.

Anthony J. Chipas, A Video Laryngoscope, How easy is it to use? How affordable to practice?, Outpatient Surgery Magazine, Jan. 2009, 4 pages.

E. B. Liem, et al., New options for airway management: intubating fibreoptic stylets, The Board of Management and Trustees of the British Journal of Anesthesia©, 2003, 11 pages.

Ken Yanagisawa, "How I Do It"—Head and Neck and Plastic Surgery, Color Photography of Video Images of Otolaryngological Structures Using a 35 mm SLR Camera, Laryngoscope 97, Aug. 1987, 2 pages.

J. E. Smith, et al., Teaching Fibreoptic Nasotracheal Intubation With and Without Closed Circuit Television, British Journal of Anesthesia, 1993, pp. 206-211.

Pentax Corporation, Airway Scope AWS-S100, Rigid Video Laryngoscope for Intubation, Jan. 6, 2006, 4 pages.

Coopdech, Video Laryngoscope Portable VLP-100 Specifications, webpage, Aug. 2009, 2 pages.

Truview EV02 New generation intubation devices, Truphatek.com webpage, Jan. 2007, 2 page.

Truview Premier Intubation Trainer Kit, webpage, Feb. 4, 2010, 2 pages.

Pentax Corporation, Fast Accurate Portable Airway Scope, LMA North America, Inc., May 31, 2006, 19 pages.

(56) References Cited

OTHER PUBLICATIONS

LMA North America, Inc., Introducing the McGRATH® Video Laryngoscope, Jan. 2008, 2 pages.

LMA North America, Inc., LMA CTrach™, Product Literature, May 31, 2006, 2 pages.

Verathon Medical, GlideScope® Video Laryngoscopes Product Line, May 2006, 14 pages.

International Search Report and Written Opinion for PCT Application No. PCT/US2010/058226, Jun. 1, 2011, 16 pgs.

* cited by examiner

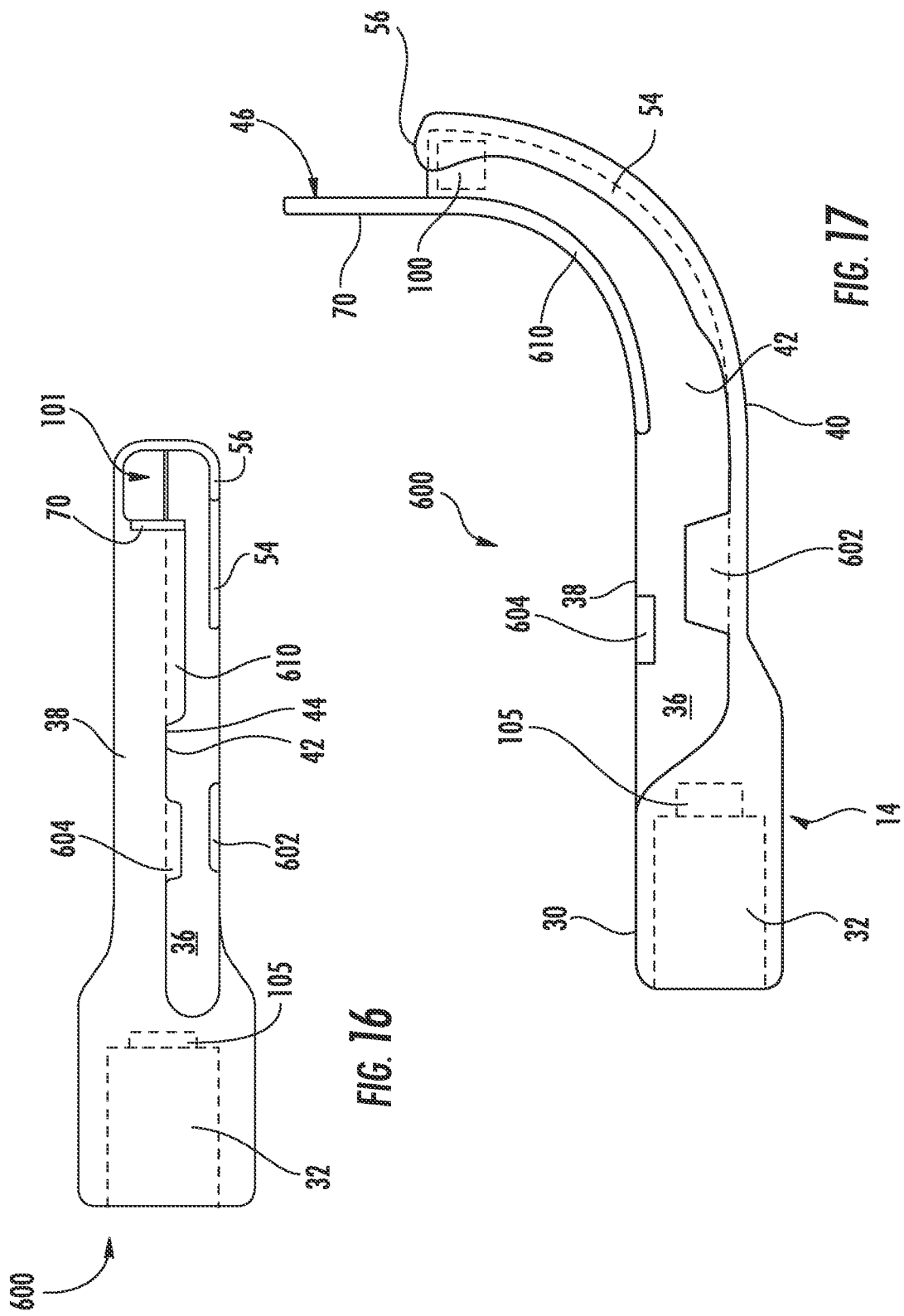

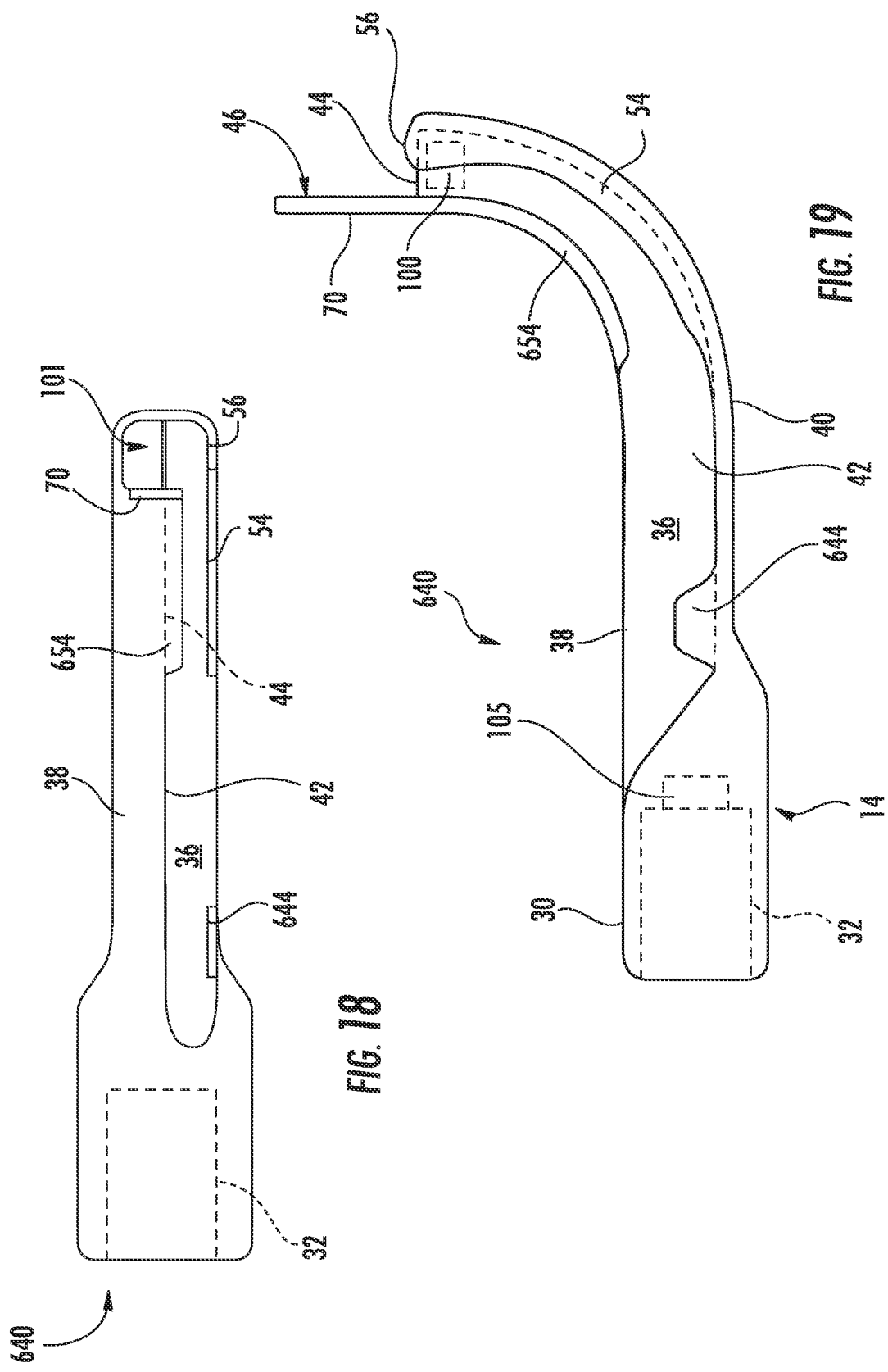

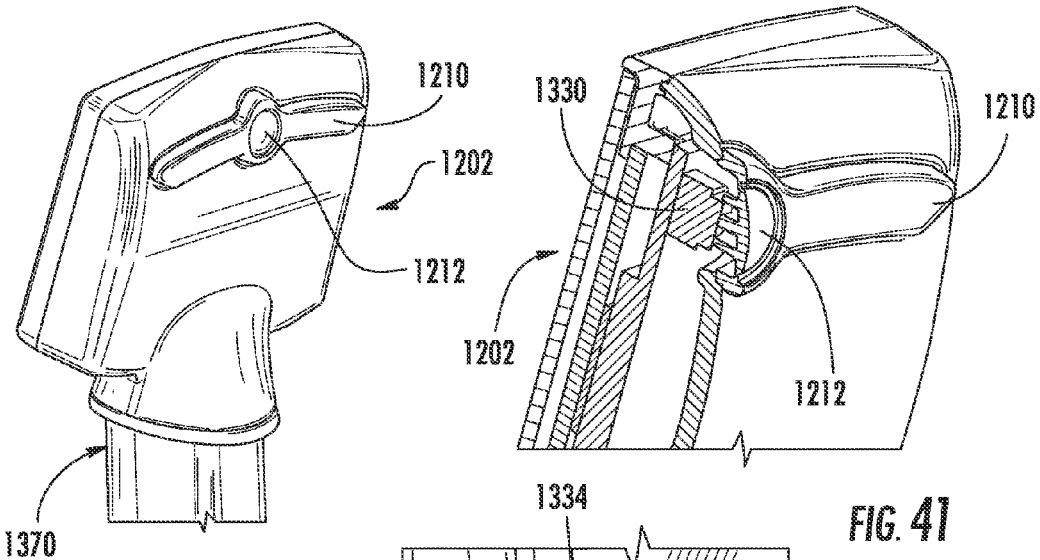
FIG. 40
FIG. 41
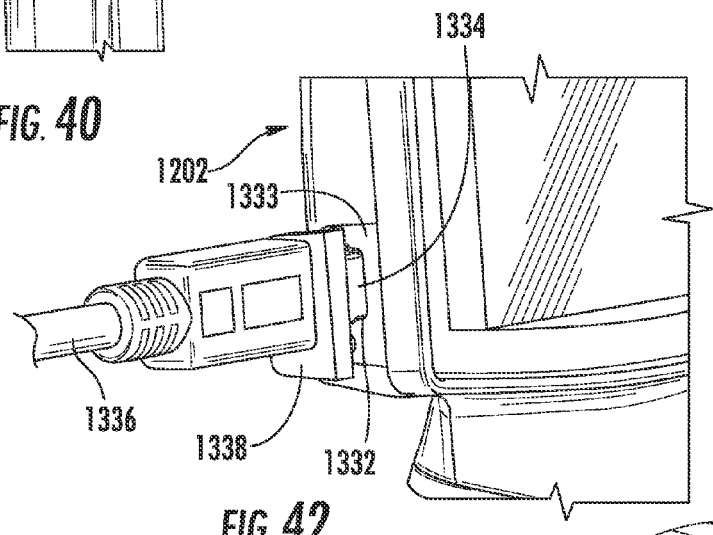
FIG. 42
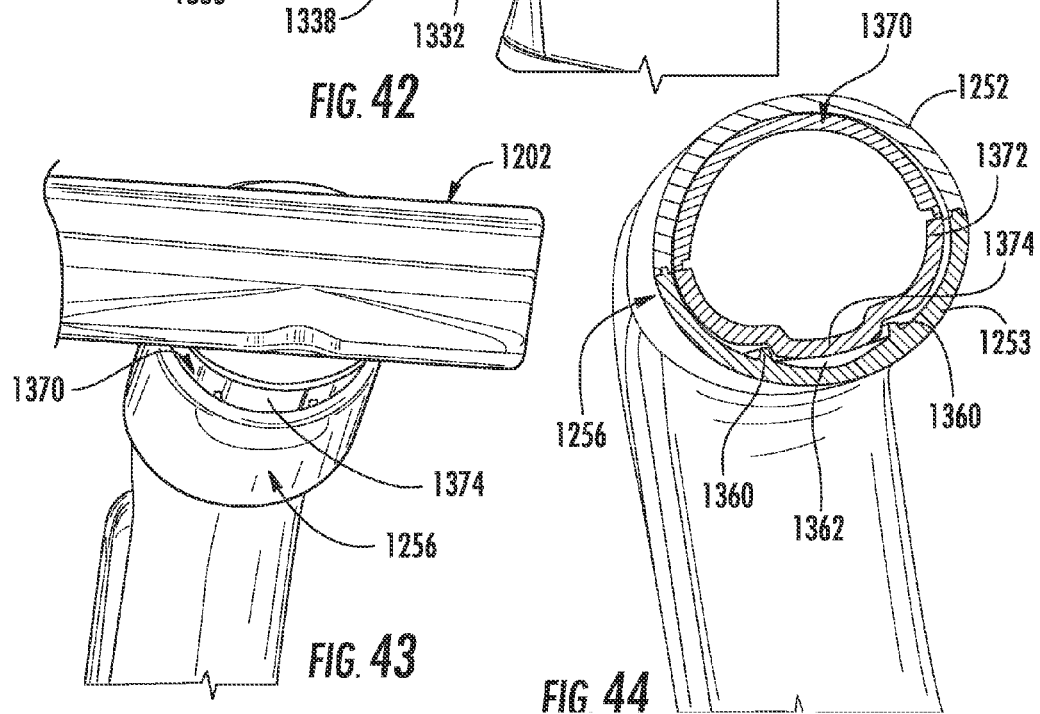
FIG. 43
FIG. 44

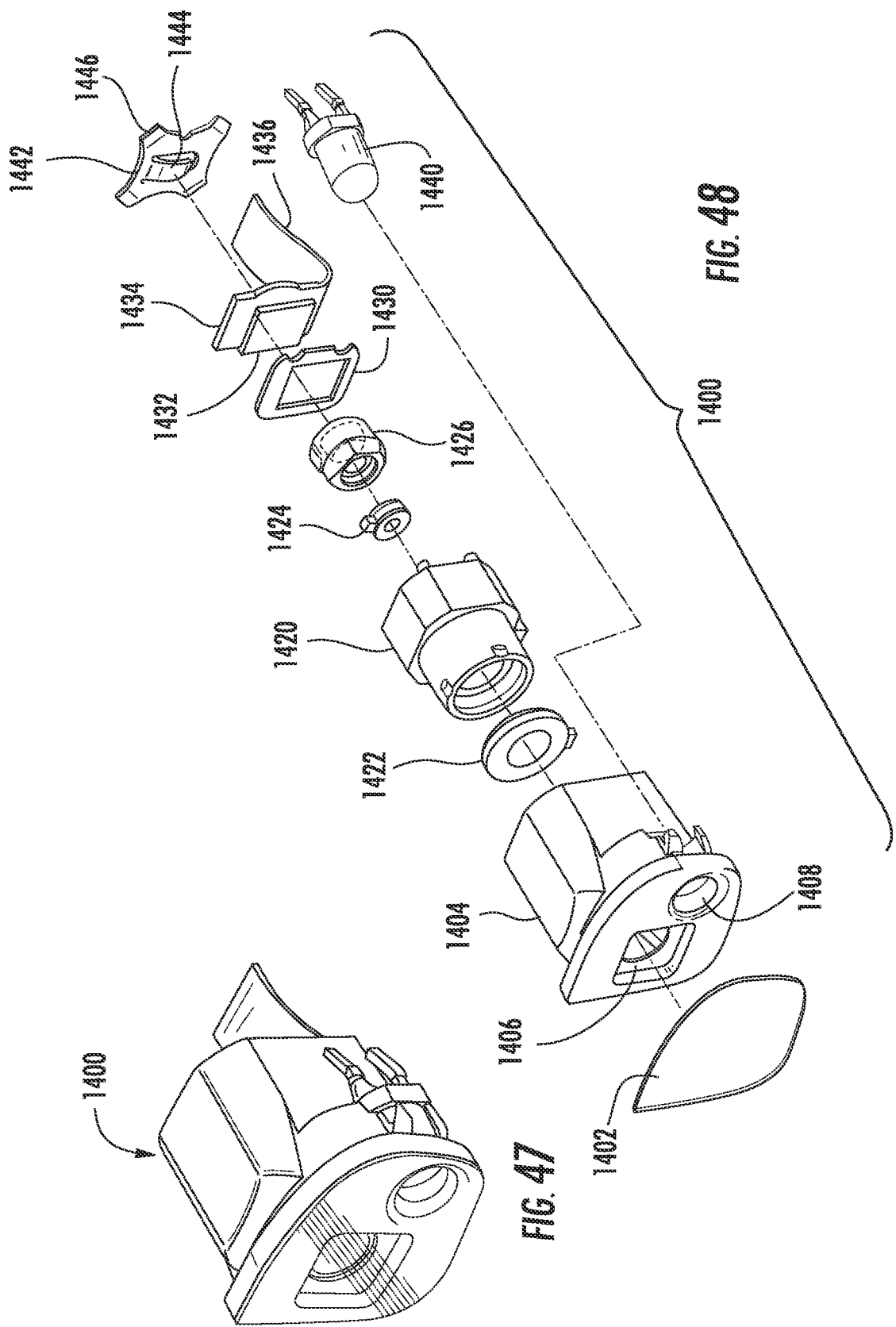

VISUALIZATION INSTRUMENT

CROSS-REFERENCE TO RELATED APPLICATIONS

This application claims the benefit of priority from U.S. patent application Ser. No. 61/314,058 entitled INTUBATION INSTRUMENT WITH VISUALIZATION FEATURES filed on Mar. 15, 2010 and U.S. patent application Ser. No. 61/265,330 entitled INTUBATION SYSTEM WITH ELASTOMERIC FEATURES filed on Nov. 30, 2009, the disclosures of which are expressly incorporated by reference herein in their entirety.

STATEMENT REGARDING FEDERALLY SPONSORED RESEARCH OR DEVELOPMENT

This invention was made with government support under Award W81XWH-06-1-0019 awarded by the U.S. Army. The government has certain rights in the invention.

FIELD OF THE DISCLOSURE

The present disclosure relates generally to a system including a visualization instrument comprising a camera to view an internal space and, more particularly, to a visualization instrument comprising a camera to examine the interior of a patient.

BACKGROUND

Visualization instruments include endoscopes, laryngoscopes, borescopes and other medical instruments designed to look inside the body of a patient. Medical visualization instruments are used in a multitude of medical procedures including laryngoscopy, rhinoscopy, bronchoscopy, cystoscopy, hysteroscopy, laparoscopy, arthroscopy, etc. Visualization instruments are also used in non-medical applications such as to investigate the internal structures of machines, buildings, and explosive devices. Laryngoscopes are used to obtain view of the vocal folds and the glottis to perform noninvasive tracheal intubations. A conventional rigid laryngoscope consists of a handle with a light source and a blade. Direct laryngoscopy is usually carried out with the patient lying on his or her back. The laryngoscope is inserted into the mouth, typically on the right side, and pushed towards the left side to move the tongue out of the line of sight and to create a pathway for insertion of an endotracheal tube. The blade may be lifted with an upwards and forward motion to move the epiglottis and make a view of the glottis possible. Once the laryngoscope is in place, the endotracheal tube may be inserted into the pathway. The blade may be provided with guide surfaces to guide the insertion of the endotracheal tube. Laryngoscopes may be outfitted with illumination devices and optical devices to provide views of the vocal cords externally of the patient's body. Optical devices include lenses, mirrors, prisms and fiberoptic fibers, all adapted to transfer an optical image. Imaging devices may also be provided to capture the optical images and display the optical images in high definition display monitors.

Stylets and other visualization instruments have also been developed. Each instrument has its own limitations such as, for example, fogging, insufficient lighting to produce a good optical image, inability to project images remotely, additional procedural steps to insert the endotracheal tube, and cost. As difficult intubations may be performed remotely from a hospital, such as at the scene of an accident or military battle, it would be desirable to provide emergency responders and others affordable equipment necessary to perform field intubations. It would be desirable to provide visualization instruments which may be discarded after a single or a limited number of uses.

SUMMARY OF THE DISCLOSURE

A visualization instrument and a method of using the visualization instrument are disclosed herein. The visualization instrument is insertable into a space to capture images representing internal views of the space. The visualization instrument comprises an insertable portion supporting an imaging sensor and a video device configured to display images corresponding to views captured by the imaging sensor.

In one exemplary embodiment of the present disclosure, a visualization instrument is provided. The visualization instrument comprising a display device; an imaging assembly including a camera and a lens; the camera including an imaging sensor, an imaging support having a distal surface and an optical cavity, the optical cavity defining a cavity opening in the distal surface, the lens and the camera sealed within the optical cavity to keep the optical cavity dry, the camera outputting a digital image stream corresponding to a plurality of views obtained through the lens; a handle portion detachably coupled to the display device; a self-contained energy source supported by one of the handle portion and the display device; and an insertable portion coupled to the handle portion and insertable into the patient, the insertable portion having a distal cavity with a distal opening at a distal end thereof, the imaging assembly received by the distal cavity through the distal opening, the imaging assembly electronically coupled to the display device when the insertable portion is coupled to the handle portion and the handle portion is coupled to the display device to present images corresponding to the plurality of views with the display device.

In a further example, the insertable portion further comprises an anterior wall and a medial wall, the anterior wall and the medial wall defining a guide pathway adapted for guiding a tube into a patient, the guide pathway adjacent a side of the medial wall and the distal cavity adjacent an opposite side of the medial wall, the anterior wall having a tip portion extending distally beyond the medial wall, the tip portion including a textured surface adapted to engage a tissue of the patient. In another variation thereof, the textured surface includes a plurality of ridges arranged in a regulated pattern. In a further variation thereof, the plurality of ridges are longitudinally aligned. In yet another variation thereof, the textured surface has a first coefficient of friction measured in a first direction and a second coefficient of friction measured in a second direction different from the first direction. In a further variation thereof, the tip portion includes a longitudinally aligned wall portion.

In yet a further example, the insertable portion comprises an elongate tubular member. In a variation thereof, the elongate tubular member is malleable. In another variation thereof, the elongate tubular member is steerable, further comprising a steering mechanism supported by the handle portion.

In another example, the visualization instrument further comprises a translucent cover attached to the distal surface, the translucent cover including an anti-fog coating.

In a further example, the visualization instrument further comprises a second lens and a camera barrel having a barrel cavity, the lens positioned between the distal surface and the camera barrel when the camera barrel is received by the optical cavity, and the second lens received by the camera barrel and positioned between the lens and the camera.

In a yet further example, the visualization instrument further comprises a motion sensor detecting motion of the display device and disabling presentation of the images when motion is not detected during a predetermined amount of time.

In another example, the camera forms the digital image stream using radiation having wavelengths ranging between 10 nanometers and 14,000 nanometers. In a variation thereof, the elongate tubular member is malleable. In another variation thereof, the camera forms the digital image stream using radiation having wavelengths in the visible light spectrum.

In yet another example thereof, further comprising a distal tip, the distal tip extends distally beyond the lens, the distal tip having a textured surface operable to displace the glottis of the patient.

In a further example thereof, further comprising a distal tip extending distally beyond the lens and a processing device, the distal tip includes a use indicia positioned within the field of view of the lens and operable to determine a use state of the insertable portion, wherein the processing device disables presentation of the images when the use state indicates prior uses exceed a permitted number of uses.

In a further example thereof, further comprising a distal tip extending distally beyond the lens, the distal tip includes flexural strengthening features to reduce flexure of the distal tip by at least 5% when the distal tip engages the patient's tissue including a longitudinal wall.

In another exemplary embodiment of the present disclosure, a visualization instrument provided. The visualization instrument comprising a display device; a lens; a camera including an imaging sensor, the camera outputting a digital image stream corresponding to a plurality of views obtained through the lens; a handle portion detachably coupled to the display device; a self-contained energy source supported by one of the handle portion and the display device; an insertable portion coupled to the handle portion and insertable into the patient, the insertable portion having a distal cavity at a distal end thereof receiving the lens and the camera, the camera electronically coupled to the display device when the insertable portion is coupled to the handle portion and the handle portion is coupled to the display device to present images corresponding to the plurality of views with the display device; and a use indicia located in one of the handle portion and the insertable portion, the use indicia operable to determine prior uses of the insertable portion and to disable presentation of the images when the prior uses exceed a permitted number of uses.

In one example thereof, the permitted number of uses is one. In another example thereof, the use indicia provides information regarding environmental variables including at least one of temperature and humidity. In a further example thereof, the use indicia comprises a single-use fuse.

In yet another example, the visualization instrument further comprises a processing device cooperating with the use indicia to determine the prior uses. In an example thereof, the instrument further comprises a sensing device electronically coupled to the processing device and sensing the use indicia to determine the prior uses. In another example thereof, the instrument further comprises an image sensor identifier, wherein the processing device determines the prior uses based on the image sensor identifier. In a variation thereof, the image sensor identifier is stored in the camera. In another variation, further comprising an electronic device storing the image sensor identifier, the electronic device is supported by one of the handle portion and the insertable portion and electronically coupled to the processing device when the insertable portion is coupled to the display device.

In a further example, the insertable portion comprises an elongate tubular member. In a variation thereof, the elongate tubular member is malleable. In another variation, the elongate tubular member is steerable, further comprising a steering mechanism supported by the handle portion.

In yet another example, further comprising a processing device, a camera identifier, a data storage device, and a plurality of camera identifiers stored in the data storage device, the processing device compares the camera identifier to the plurality of camera identifiers to find a match and disables presentation of the images if the match is not found.

In a further exemplary embodiment of the present disclosure, a visualization partially insertable into a patient is provided, the visualization instrument comprising an insertable portion having guiding means for guiding insertion of a tube into a patient; attachment means for detachably coupling a display device to the insertable portion; imaging means for capturing a plurality of images corresponding to a field of view of the imaging means and outputting a digital image stream operable to present corresponding images with the display device; and use tracking means for disabling presentation of the corresponding images when the insertable portion has been used more than a permitted number of uses.

In another exemplary embodiment of the present disclosure, a visualization kit is provided. The visualization kit comprising a first component insertable into an oral cavity of a patient, the first component including a first camera operable to transmit first images of the oral cavity; a second component different from and interchangeable with the first component, the second component including a second camera operable to transmit second images; a third component detachably attachable to the first component and the second component and sized to be held by a hand of a user, the third component including a viewable screen and being communicatively coupled to the first camera when the third component is attached to the first component and to the second camera when the third component is attached to the second component; wherein the viewable screen presents images corresponding to one of the first images and the second images. In one example thereof, the first component comprises a guide pathway adapted to guide insertion of a tube into the oral cavity and the second component comprises a stylet.

In yet another exemplary embodiment of the present disclosure, a visualization method is provided. The visualization method comprising the steps of providing an insertable component having a camera; detachably coupling a display support component to the insertable component, the display support component sized to be held by a hand of a user and including a display device, the display support component being communicatively coupled to the camera when the display support component is coupled to the insertable component; inserting the insertable component into a target space; capturing with the camera a plurality of views corresponding to a field of view of the camera; presenting with the display device a plurality of images corresponding to the plurality of views; aligning the field of view with a target within the target space; removing the insertable component from the target space; detaching the display support component from the insertable component; tracking uses of the insertable component; and disabling presentation of the plurality of images when the insertable portion has been used more than a permitted number of uses. In an example thereof, the method further comprises the step of discarding the insertable component. In a variation thereof, the step of tracking uses comprises sensing a use indicia. In a further variation thereof, the step of tracking uses comprises storing a use indicia after use of the insertable component.

In a further example thereof, the display device includes a display side and an opposite side opposite the display side, the display support component further comprising a rest surface and a switch, the rest surface and the switch disposed on the opposite side, further comprising the step of laying the display support component to rest on the rest surface without actuating the switch.

In another example thereof, the method further comprises the steps of comparing with a processing device a camera identifier to a plurality of camera identifiers stored in a memory device to find a match, and disabling presentation of the plurality of images if the match is not found.

In a further exemplary embodiment of the present disclosure, a visualization instrument configured to intubate a patient is provided. The visualization instrument comprising a display device including a display driver and a display; an imaging assembly having an image sensor, a transparent cover, a plurality of lenses between the image sensor and the transparent cover, and an illumination device illuminating a cavity of the patient, the imaging assembly configured to transfer an image stream representing views of the cavity to the display device; a control component including a processor, a memory, and a program embedded in the memory, the processor receiving the data stream from the imaging assembly, transforming the data stream into a second data stream, and providing the second data stream to the display driver to show the views of the cavity on the display; a housing coupled to the display device and having a first connector configured to receive the second data stream from the control component; and an insertable portion having a proximal cavity configured to receive the housing and a distal cavity configured to receive the imaging assembly, the insertable portion also including a second connector configured transfer the first image stream from the imaging assembly through the first connector to the control component, the insertable portion further including a passageway configured to guide insertion of an elongate tubular component into the cavity, wherein the imaging assembly is configured to capture in the first image stream images of a distal end of the tubular component as the tubular component slides through the guide; an identification source located in the insertable portion; and a sensor communicatively coupled with the control component and configured to sense an identification signal from the identification source, the identification signal operable to ascertain a prior use of the insertable portion, the control component being configured to detect the prior use based on the identification signal and to prevent operation of the imaging assembly upon detection of the prior use.

In another exemplary embodiment of the present disclosure, a visualization instrument is provided. The visualization instrument comprising a display device including a display driver and a display; an imaging assembly having an image sensor, a transparent cover, a lens between the image sensor and the transparent cover, and an illumination device illuminating a cavity of the patient, the imaging assembly configured to transfer an image stream representing views of the cavity to the display device; a control component including a processor, a memory, and a program embedded in the memory, the processor receiving the data stream from the imaging assembly, transforming the data stream into a second data stream, and providing the second data stream to the display driver to show the views of the cavity on the display; a housing coupled to the display device and having a first connector configured to receive the second data stream from the control component; and an insertable portion having a proximal cavity configured to receive the housing and a distal cavity configured to receive the imaging assembly, the insertable portion also including a second connector, a passageway, and a distal tip, the second connector configured to transfer the first image stream from the imaging assembly through the first connector to the control component, the passageway configured to guide insertion of an elongate tubular component into the cavity, and the distal tip engaging a glottis of a patient, the distal tip having a lateral wall extending distally beyond the distal cavity and a textured surface configured to engage the glottis, wherein the imaging assembly is configured to capture in the first image stream images of a distal and of the tubular component as the tubular component slides through the guide.

In yet another exemplary embodiment of the present disclosure, a visualization instrument is provided. The visualization instrument comprising a display device including a display driver and a display; an imaging assembly having an image sensor, a transparent cover, a lens between the image sensor and the transparent cover, and an illumination device illuminating a cavity of the patient, the imaging assembly configured to transfer an image stream representing views of the cavity to the display device; a control component including a processor, a memory, and a program embedded in the memory, the processor receiving the data stream from the imaging assembly, transforming the data stream into a second data stream, and providing the second data stream to the display driver to show the views of the cavity on the display; a housing coupled to the display device and having a first connector configured to receive the second data stream from the control component; and an insertable portion having a proximal cavity configured to receive the housing and a distal end having a distal cavity configured to receive the imaging assembly, the insertable portion also including a second connector, a passageway, and a distal tip, the second connector configured to transfer the first image stream from the imaging assembly through the first connector to the control component, passageway configured to guide insertion of an elongate tubular component into the cavity, and the distal tip engaging a glottis of a patient, the distal tip having a lateral wall extending distally beyond the distal cavity and a textured surface configured to engage the glottis, wherein the distal tip exhibits a curvature perpendicularly to a length of the insertable portion and includes at least a portion of a ridge parallel to the length of the insertable portion, the curvature and the ridge enhancing the flexural strength of the distal tip by at least 5%.

In a further exemplary embodiment of the present disclosure, a visualization instrument configured to intubate a patient is provided. The visualization instrument comprising an insertable component including a camera, at least two lenses, and an illumination device to illuminate the oral cavity of the patient when the insertable component is inserted, at least partially, into the oral cavity, the insertable component being configured to guide insertion of a tube through the vocal cords of the patient, and the camera being mounted on the insertable component so as to capture images of a distal end of the tube as the tube enters the vocal cords; a reusable component including a display device and a video processing portion, the reusable component being removably attachable to the insertable component; an identification insignia on the insertable component; and a sensor supported by the reusable component and operable to sense the identification insignia, wherein the reusable component determines an identity data of the insertable component based on the identification insignia, and determines a status of the insertable component by comparing the identity data to a plurality of identity and status data corresponding to a plurality of insertable components.

The features of this invention, and the manner of attaining them, will become more apparent and the invention itself will be better understood by reference to the following description of embodiments of the invention taken in conjunction with the accompanying drawings.

BRIEF DESCRIPTION OF THE DRAWINGS

FIGS. 16 and 17 are elevation and plan views of a further embodiment of an insertable portion of a visualization instrument;

FIGS. 18 and 19 are elevation and plan views of yet another embodiment of an insertable portion of a visualization instrument;

FIGS. 40 to 46 are partial perspective views of features of the instrument of FIGS. 34 and 35; and FIGS. 47 and 48 are perspective and views of an imaging system operable with a visualization instrument.

Figure 1:
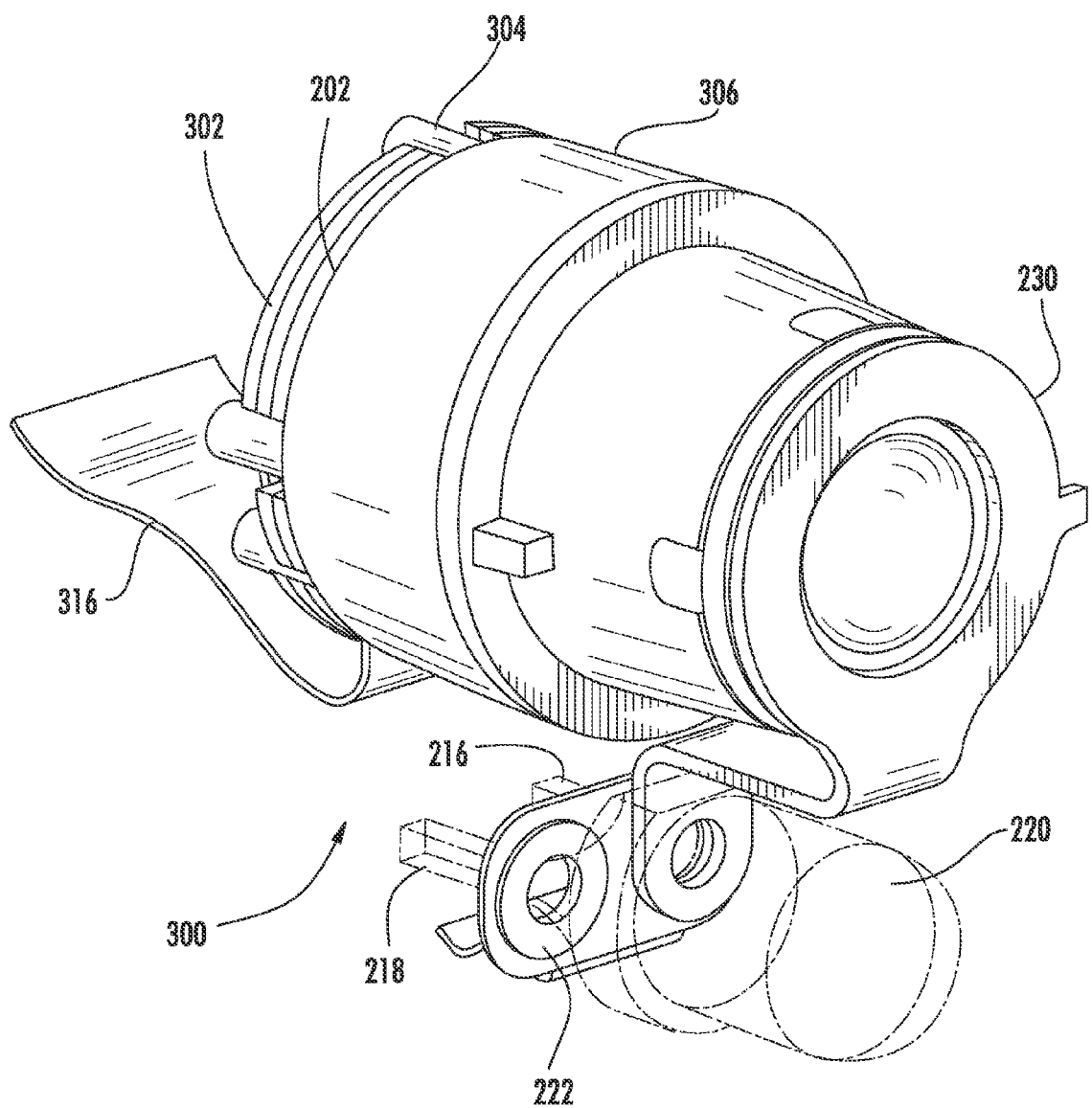
FIGS. 1 and 2 are perspective views of an embodiment of an imaging assembly.

Corresponding reference characters indicate corresponding parts throughout the several views. Although the drawings represent embodiments of the present invention, the drawings are not necessarily to scale and certain features may be exaggerated to better illustrate and explain the embodiments. The exemplifications set out herein illustrate embodiments of the invention in several forms and such exemplification is not to be construed as limiting the scope of the invention in any manner.

DETAILED DESCRIPTION

The embodiments of the disclosure discussed below are not intended to be exhaustive or limit the invention to the precise forms disclosed in the following detailed description. Rather, the embodiments are chosen and described so that others skilled in the art may utilize their teachings.

A visualization instrument, and a method of using the instrument, are disclosed herein. In one embodiment of the visualization instrument, the visualization instrument comprises a display screen and a display screen support portion removably and electrically coupled to an insertable portion including an imaging system to acquire images of an internal space. Exemplary visualization instruments include endoscopes, laryngoscopes, and stylets. The display screen support portion and the display screen may be integrally constructed and may be reusable or disposable. In various embodiments described below, a unitary component comprising the display screen and the display screen support portion is referred to as a reusable portion denoting that in many instances it is possible, although not necessary, and perhaps desirable for economic reasons, to reuse the display screen and electronic components relating thereto. In one variation thereof, the visualization instrument transfers images to a remote display. In one example thereof, the reusable portion includes a housing received in a proximal cavity of a handle coupled to the insertable portion. The display device is supported by the housing. An anti-glare coating or layer may be provided on the display surface.

In another embodiment of the visualization instrument, the insertable portion comprises a passageway or guide pathway configured to guide insertion of an elongate tubular component, e.g., an airway device, endotracheal tube and the like, and an imaging assembly disposed on or in the distal end of the insertable portion. The imaging assembly captures images of the patient which are shown with the display device. A distal end of the tubular component may also be visible in the images as the tubular component slides through the guide pathway towards the vocal cords. Illustrative embodiments of the reusable and insertable portions are described with reference to FIGS. 10, 11, 16-19, 24-27, 34 and 35.

In yet another embodiment of the visualization instrument, the insertable portion comprises an elongate arm having an imaging assembly disposed in the distal end of the arm. In one example thereof, the elongate arm is coupled to a handle adapted to receive the reusable portion. In one variation of the previous example, the elongate arm forms part of a stylet. Illustrative embodiments of stylets are described with reference to FIGS. 26 and 27. In another variation thereof, the elongate arm and the handle comprise an endoscope.

In a further embodiment of the visualization instrument, an imaging cap is provided. The imaging cap comprises a handle adapted to removably receive the reusable portion and a camera to enable a user to capture external images. Additional data acquisition sensors may be coupled to the reusable portion or the imaging cap. An illustrative embodiment of the imaging cap and the sensors is described below with reference to FIG. 9. It should be understood that in any of the embodiments disclosed herein, the reusable portion may be adapted to removably receive the handle instead of the handle being adapted to removably receive the reusable portion.

In an embodiment of a visualization system disclosed herein, the visualization instruments described above are adapted to transmit images to a remote device. Exemplary embodiments of systems adapted to transmit images from the reusable portion to the remote device are described below with reference to FIGS. 7 and 8.

Advantageously, the imaging assembly may be configured to be produced at a low cost to enable the insertable portion to function as a single-use disposable device. In one embodiment, the imaging assembly comprises a support structure or camera barrel supporting a camera integrated circuit (IC), camera, or camera-chip, an illumination device, and lenses. The imaging assembly may be inserted into a cavity located in the distal end of the insertable portion. The imaging assembly may comprise a retention device, e.g., a pin, detent, resilient elastomeric filler, screw or any other fixation device configured to securely couple the imaging assembly to the distal cavity. Exemplary embodiments of imaging assemblies are described below with reference to FIGS. 1-6, 47 and 48.

Several defogging features may be provided to prevent fogging of the imaging assembly. In one embodiment, the distal surface of the most distally located lens is coated to reduce or eliminate fogging. In one example thereof, an anti-fog coating is applied to one side of a substrate and an adhesive coating is applied to the other side of the substrate. The adhesively coated side is then adhered to the distal lens surface to attach the anti-fog coating to the lens. The substrate may comprise any known combination of polymers extruded in clear thin film form. Exemplary polymers include polycarbonate, polyester based polymers, polystyrene, polyethylene, polypropylene, and other transparent polymers. A removable backing may be applied to the adhesively coated thin film to facilitate processing. The backing is then removed to expose the adhesive before application of the substrate to the lens surface. In another example, a cover plate seals the cavity and prevents lens fogging. In one variation thereof, the cover plate includes an anti-fog layer or coating on its external surface. The insertable portion may be packaged with a swab comprising $H_2O_2$ or other antifog coating agents, such that the swab wipes the lens when the insertable portion is withdrawn from the packaging. For example, the packaging may comprise a polymeric strip with a swab attached thereto. Alternatively, the adhesively and anti-fog coated substrate may be adhered to the cover plate. In a further example, defogging is achieved by coupling a heating element to the cover plate and to the power leads of an illumination device, which in one embodiment is a white light emitting diode (LED), which is driven above its nominal illumination power level to generate heat with the excess power. In another variation, an LED conducting 150 milliamps coupled to a thermal element heats the distal lens to 45 degrees Celsius in about one minute.

A commercially available camera, such as a camera used in cellular phones and personal digital assistants (PDAs), comprises an image sensor and electronic components configured to convert pixel data captured by the image sensor to image data, e.g., digital images, and to output streams of digital images in a standard format. Image sensors may comprise CCD, CMOS sensors with active or passive pixels, or other photo sensors well known in the art. Operational signals are provided to the image sensor to control its operation. Advantageously, the cost of the disposable portion is reduced further by locating the components for providing the operational signals in the reusable portion. In one embodiment, a display driver configured to receive the standard image stream and drive the display device accordingly, also comprises the components necessary to control the camera. In one example thereof, the input/output signals are provided by signal conductors, e.g., a multi-conductor flexible ribbon. In another example thereof, a control component is provided intermediate the camera and the display driver to transform the standard image stream into a differently structured image stream conforming to the size of the display device and/or transforming the standard image stream to a different format corresponding to the format required by the display driver. In a further example thereof, the operational circuits are integrated with the camera, which is configured to output a preconfigured image stream upnn the application of power, and which is usable directly by the display device. In yet another example, control components supported by the reusable portion housing provide control signals to the camera to define the size of the images output by the camera. In a further example, the image stream output by the camera is transmitted wirelessly by a wireless transmitter located in the insertion portion. In yet a further example, the wireless transmitter is integrated with the camera. In a variation thereof, the wireless transmitter is positioned in the proximal end of the insertable portion or in the distal cavity. In one example, the camera forms a digital image stream using radiation having wavelengths ranging between 10 nanometers and 14,000 nanometers. The wavelengths include the visible light, ultraviolet, and infrared spectrums. In one variation, the camera is an infrared camera. In another variation, the camera is an ultraviolet light camera. In another variation, the camera is a visible light camera.

While the embodiments of the disclosure are applicable in medical and non-medical applications, exemplary features of visualization instruments will be described below with reference to medical instruments such as laryngoscopes and stylets although the invention is not limited to medical applications and instruments.

Generally, an intubation instrument comprises a reusable portion having a display device coupled to a housing and a blade. The blade comprises a handle in a proximal end thereof spaced apart from an insertable portion located at a distal end. An imaging assembly is located at the distal end of the insertable portion. The term blade denotes a single part integrally combining a handle and an insertable portion defined by a plurality of walls as described below. In a variation thereof, the handle and the insertable portion are distinct parts that are removably attachable. A display device includes a viewing screen. The handle comprises a proximal cavity for receiving the housing and coupling the reusable portion to the blade. The insertable portion of the blade comprises an elongate passageway or pathway designed to guide insertion of a catheter, intubation tube and the like (not shown) into the larynx of a patient. The housing includes batteries and electronic circuits to receive image signals from the imaging assembly via a conductor which comprises a plurality of signal conductors and may comprise power and control conductors as well. In an alternative embodiment, the conductor is at least partially replaced with a wireless transmitter and receiver coupling the imaging assembly and the housing. The housing may comprise a control component and a connector adapted to couple with a connector of the blade to transfer images thereto. Exemplary imaging assemblies are disclosed in FIGS. 1-6. Throughout the figures, reference is made to imaging assembly 300 for exemplary purposes. Unless stated differently below, reference to imaging assembly 300 is representative and non-limiting. Any one of imaging assemblies 350, 380, 400 and variations thereof, may be used instead.

An exemplary pathway is defined by the interior surfaces of a medial wall, an anterior wall, a posterior wall, and a lateral wall. Each wall has an interior surface which is the surface adjacent to the pathway. In other embodiments, the lateral wall may extend uninterrupted from the proximal to the distal end of the blade or may be configured with more or fewer wall portions. A distal tip extends from the anterior wall beyond the end of the medial wall and comprises a surface which is configured to contact the patient to move the epiglottis and expose the vocal cords.

Figure 2:
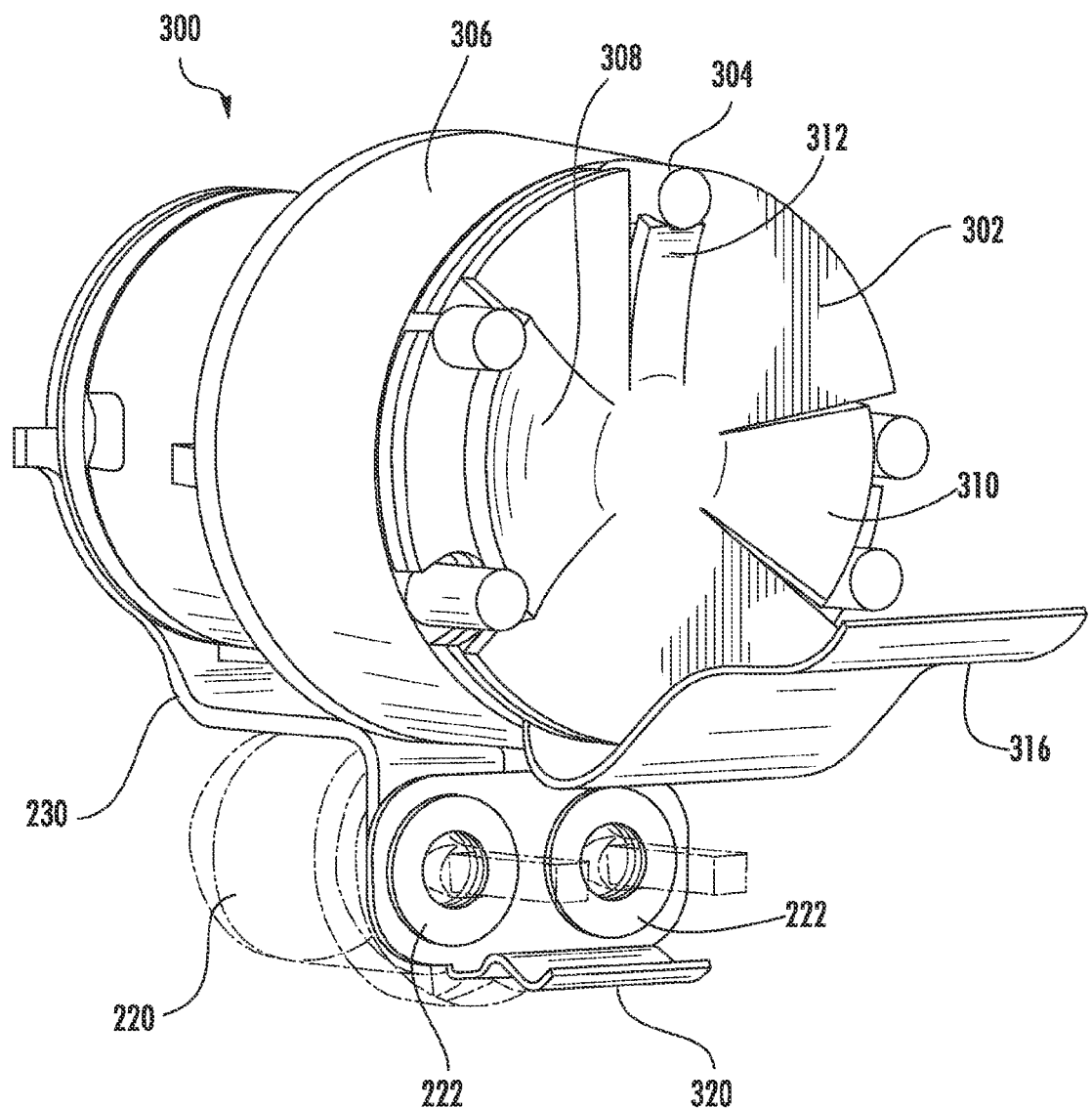

An imaging assembly comprises a plurality of lenses supported by a camera barrel. FIGS. 1 to 6 illustrate embodiments of imaging assemblies. FIGS. 1 and 2 are perspective views of an imaging assembly 300. As shown in FIG. 1, a heating element 230 supports an illumination device 220 which comprises an LED powered by connectors 216 and 218. The LED may be over-driven to provide power in excess of that which is necessary to produce the maximum illumination output of the device. A pair of washers 222 thermally insulate heating element 230. The excess power generates heat which is transferred to heating element 230 to reduce fogging. A camera barrel 306 supports a lens 210, a lens 212 and a lens 214. Images corresponding to spaces viewable by distal lens 210 are sensed by a camera 202 (shown in FIG. 3) which comprises a sensing array and circuitry to output an image stream comprising pixel data. A plurality of prongs 304 extend proximally from camera barrel 306. In this embodiment, a circuit board including camera 202 comprises a plurality of notches configured to fit around prongs 304. A pressure plate 302 comprising tabs 308, 310 and 312 (shown in FIG. 2) is configured to press-fit against prongs 304 to secure camera 202 against camera barrel 306. A tab 316 is positioned between camera barrel 306 and pressure plate 302 and also secured by it. Furthermore, an end tab 320 may optionally be provided and secured by pressure plate 302 to press against the distal cavity to secure imaging assembly 300. In an alternative embodiment, camera 202 fits inside camera barrel 306 and is not supported by pressure plate 302.

Figure 3:
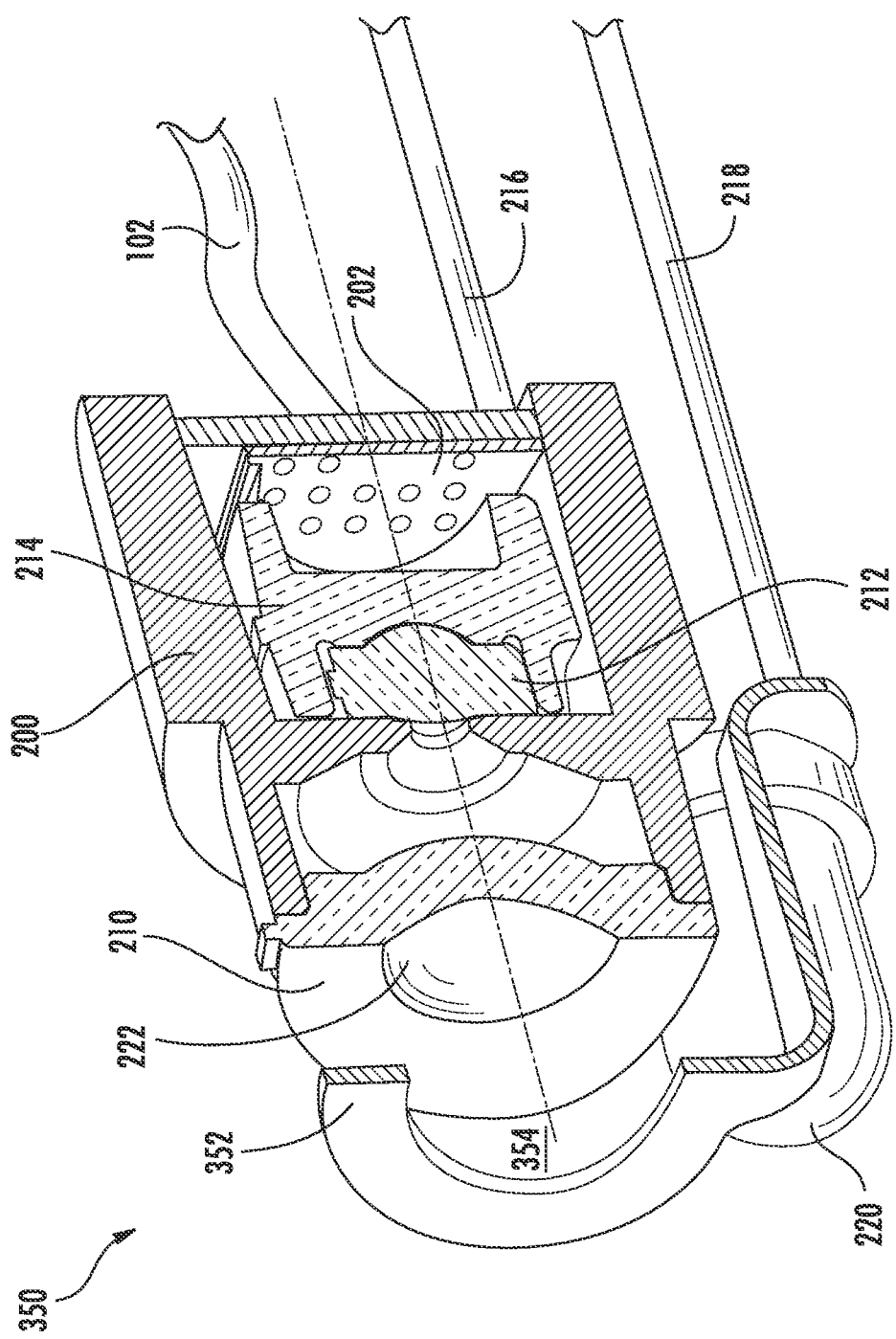
FIGS. 3 and 4 are cross-sectional perspective and plan views of a further embodiment of an imaging assembly.
Figure 4:
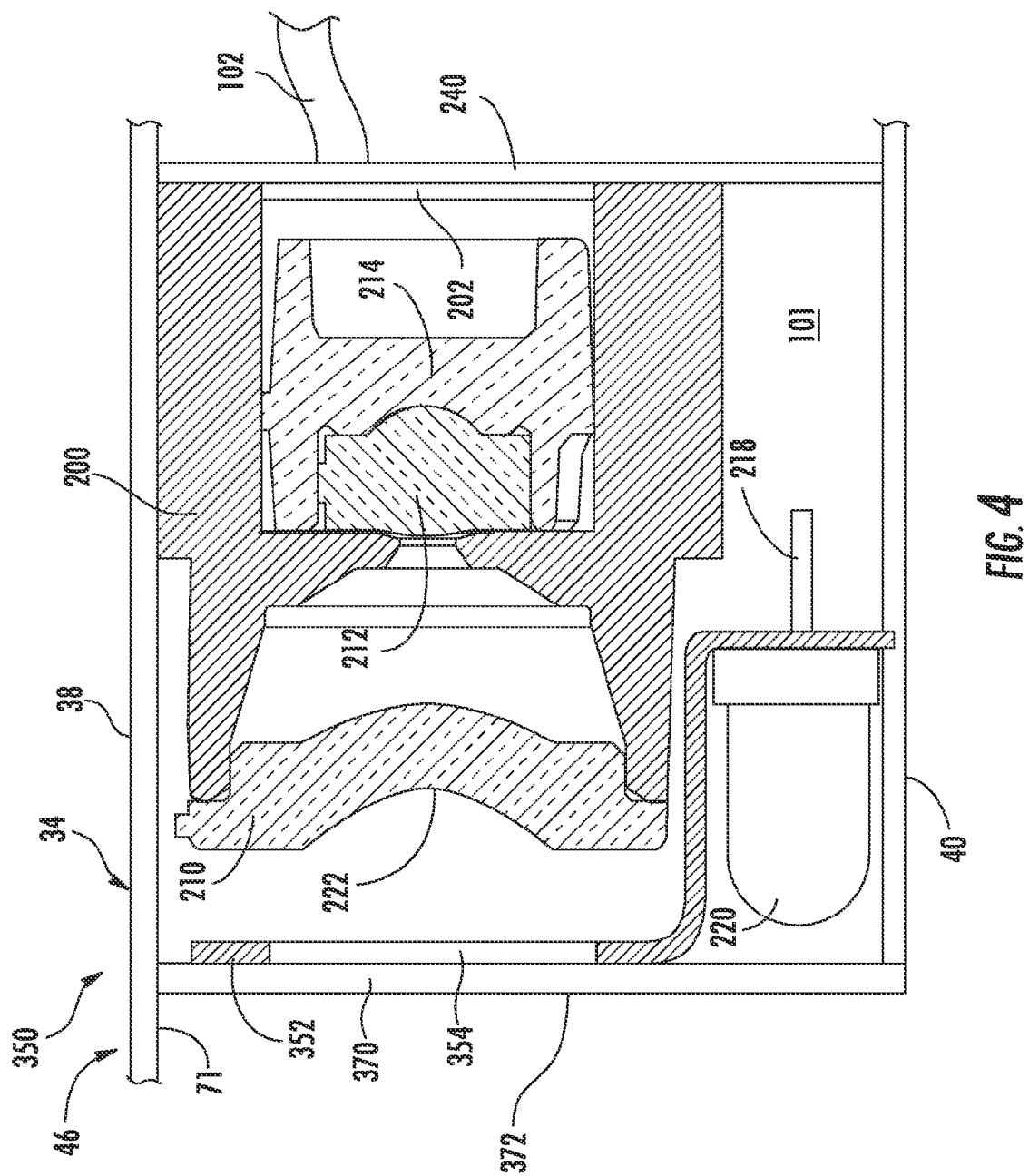

FIGS. 3 and 4 are cross-sectional perspective and plan views of an imaging assembly 350 comprising a heating element 352 having an orifice 354, and a cover 370 having a distal surface 372. Heating element 352 supports illumination device 220. A camera barrel 200 also supports camera 202 and is supported by support element 240 between an anterior wall 34 and a posterior wall 40 at the distal end of the insertable portion. Heating element 352 heats cover 370 to prevent fogging or to defog. Alternatively or additionally, a surface 372 may be covered with an anti-fog coating or layer. A portion of a distal tip 46 is shown in FIG. 4 illustrating a portion of surface 71 in which a ridge or another "landing strip" landmark may be provided for viewing by the imaging assembly.

In a further embodiment of a visualization instrument, imaging features are provided on a surface of the insertion portion to indicate its orientation relative to the space viewed by the camera as observed in the images. In one example thereof, the imaging feature is a landmark, illustratively a ridge 48 (shown in FIGS. 10 to 13). An image object corresponding to ridge 48 is displayed in the image stream and, further, the position and shape of the image object are adjusted to reflect the angular orientation of imaging assembly 300 relative to the center line of the blade. For example, if imaging assembly 300 is oriented at 15 degrees, the image object may be extracted from the image and replaced at a 15 degree offset. In another example thereof, a "landing strip", scalloped edge, a name or label, an arrow, line or other orientation demarking symbol is provided near ridge 48 which, when viewed in the display device, enable a practitioner to easily determine how to orient the intubation instrument to direct the endotracheal tube toward the vocal cords which are visible in the image. In a variation thereof, gages, bar graphs, compasses, and other digitally generated orientation images are provided in the images to indicate the direction of movement of the instrument. The orientation images may be generated by identifying vocal cord landmarks in the image stream, comparing the landmarks to the image object, e.g., the image of ridge 48, and then determining the amount of change required in each axis of motion to align the tube in the passageway with the vocal cords.

Figure 5:
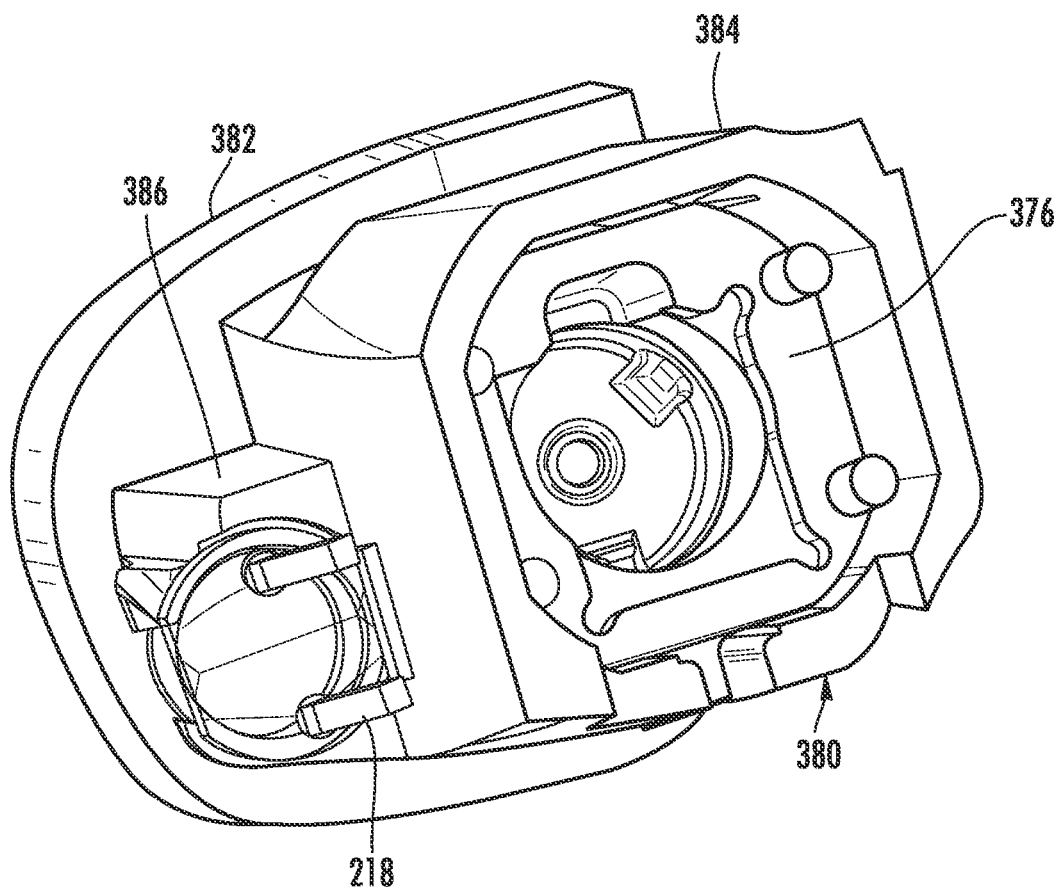
FIGS. 5 and 6 are perspective proximal and distal views of yet another embodiment of an imaging assembly.
Figure 6:
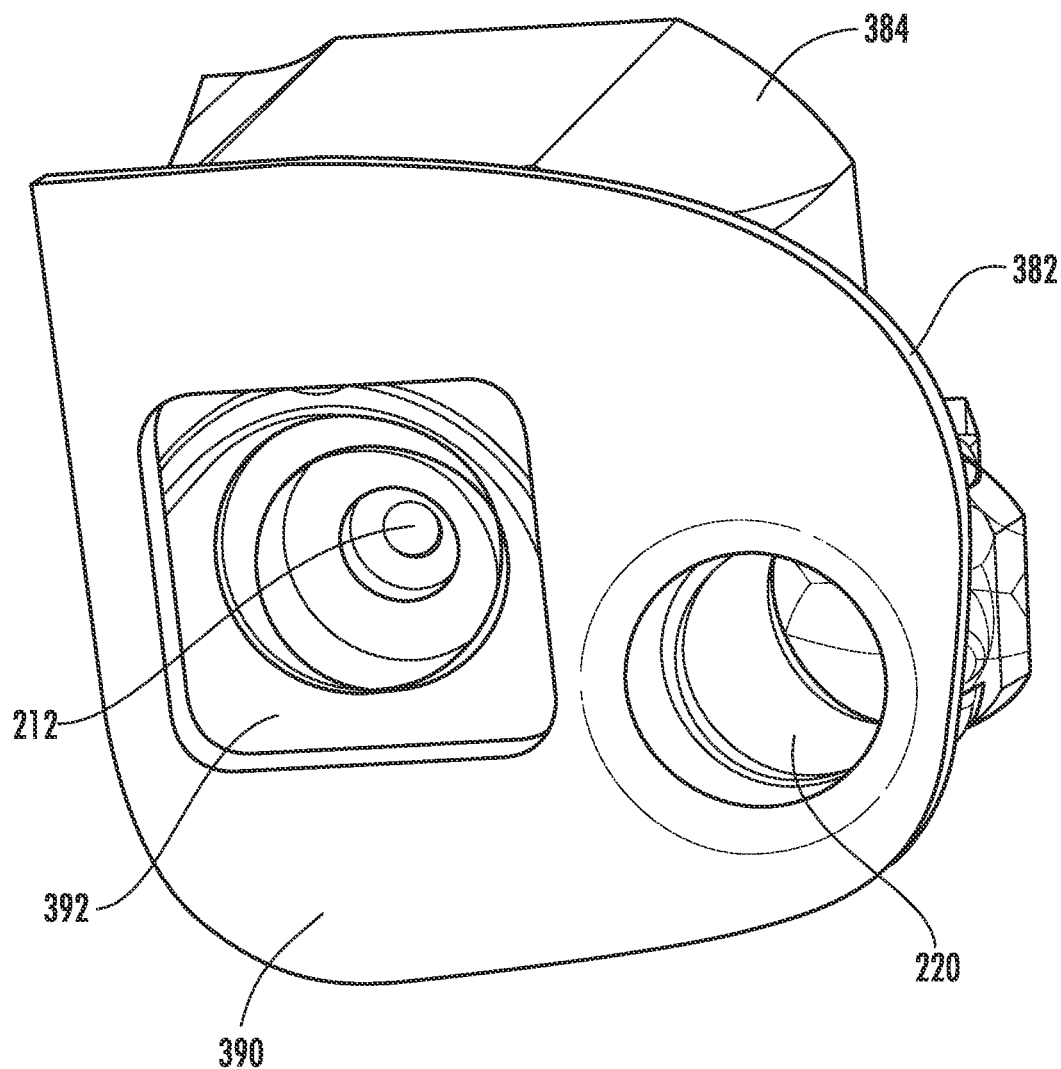

FIGS. 5 and 6 are perspective views of an imaging assembly 380. Imaging assembly 380 comprises a camera barrel 376 which supports distal lens 210, lens 212, lens 214, and camera 202. Camera barrel 376 is similar to camera barrel 306 since both have prongs adapted to receive a pressure plate which may be used to hold the camera in place. Camera barrel 376 is supported by a camera holder 384 which comprises a distal wall 382 and a support structure 386 having a cavity receiving illumination device 220 therein. A distal wall 382 comprises a distal face 390 and an aperture 392. An anti-fog film or layer coated with antifogging composition may be attached to distal face 390. Alternatively, distal wall 382 may comprise a translucent or transparent material without aperture 392, attachable to camera holder 384. At least a portion of camera holder 384 fits within the distal cavity of the insertable portion of the visualization instrument. It may snap-fit into place or be adhesively bonded to ensure retainment therein. Camera holder 384 may be attached to the insertable portion or imaging cap with adhesive, heat stakes, ultrasonic welds, tongue-and-groove arrangement, or any other suitable means. Similar attachment methods may be used to attach an anti-fog cover to the insertable portion or imaging cap.

In a further embodiment of a camera assembly, the prongs extend from the proximal end of camera holder 384 rather than from the proximal end of camera barrel 376. Camera barrel 376 slides into a cavity in the camera holder from the proximal end of the camera holder. Then, the circuit board supporting the camera is attached. The pressure plate is attached last. The pressure plate engages the prongs of the camera holder thereby holding the camera barrel and the camera in place. The camera can be mounted onto the camera barrel in any other manner. Advantageously, in this embodiment the size of the circuit board holding the camera can be reduced since it no longer has to engage the prongs. Of course, the camera can be supported by any other means alternative to a circuit board.

In one example of the present embodiment, the camera supplies a first image stream which is 8-bits wide. The resolution of the camera is 640×480 (VGA) pixels per frame. There are 30 frames per second. The data format is 2 bytes per pixel (i.e., the no called YUV (4:2:2) format). Intensity Y is specified at every pixel, color information U or V every second time. A FPGA is programmed to convert the data stream to a second image stream with a format compatible with the display device which comprises an OLED display. In an alternative embodiment, the camera data is provided to the video processing chip, and the video processing chip, after adding information such as colors, symbols or other information, outputs a video stream to the FPGA for the FPGA to convert to the VGA format. The display resolution is 320×240 (QVGA) pixels per frame, 30 frames per second. The data format, however, is RGB (6, 6, 6). This format uses a 6-bit value for red, a 6-bit value for green, and a 6-bit value for blue. There are specific well known equations for conversion from the YUV color space to the RGB color space. The FPGA implements this conversion. It also performs the conversion (e.g. dropping every second pixel) to convert from VGA to QVGA resolution. The FPGA also provides signals for writing the converted data stream into the OLED display's memory/buffer. The FPGA also sends the camera data to the NTSC/S-video conversion chip. The video chip having the video processor is capable of accepting the VGA, YUV format almost directly. The FPGA provides the necessary operational signals to load the video chip's memory. In a variation thereof, the FPGA also verifies the identity of the camera against a database of approved cameras. The FPGA extracts camera information from the camera, for example a built-in camera ID or a programmable camera ID, and checks the identity against an approved list which is periodically updated. If the camera identification is not on the approved list, the FPGA does not convert the first image stream or, optionally, inserts a warning into the second image stream to alert a practitioner that the insertable portion is not an approved device. Approval may be desirable to ensure the insertable portion meets quality specifications.

A program and data structures are embedded in the memory. The program comprises a plurality of processing sequences operable by the processor to interact with data structures containing data. Data may include parameters such as video instructions, security feature instructions, landmark patterns and the like. The reusable portion may comprise temperature and humidity sensors, and the data may thus include status information, e.g., battery charge level and number of uses, and environmental information, e.g. temperature and humidity levels. Such data may be displayed by the display device or transmitted to a remote device to assist the practitioner. Suitable alarm functions may be implemented if the environmental or battery information falls outside predetermined ranges.

In one embodiment of a visualization instrument, a first processing sequence examines the first image stream and identifies a plurality of landmarks corresponding to features of the internal space and orientation features on the insertable portion. Another processing sequence transforms the first image stream by coloring the space landmarks. A third processing sequence transforms the first image stream by coloring the orientation features. In one example, the orientation feature is a viewable marking in the distal surface of distal tip 46 or an internal surface of wall 34 (both shown in FIG. 4) and the space landmark corresponds to the shape of the vocal cords. The first image stream is thus transformed to enhance the practitioner's ability to align the intubation instrument with the vocal cords.

In another embodiment of a visualization instrument, power saving features are provided to extend the battery life of the reusable portion of the visualization instrument. Power is consumed by illumination, image display, image stream generation, and conversion of the image stream from the image sensor to the display device. In one example thereof, the reusable portion disables the display device if it detects the absence of the camera (a disengaged period). Enablement of the display device during disengaged periods may cause video display noise and frozen images which are prevented if the display is disabled during those periods.

In another example, the display device is also disabled during monitoring periods and automatically enabled if monitoring generates an alert, e.g., low battery, defective connection, high humidity and the like. In a monitoring period a practitioner may also manually enable the display device to request information. Alternatively, an inactive mode may be set which disables monitoring and thereby also disables the display device. In a variation thereof, the monitoring or the inactive mode may be determined based on the engagement or disengagement of the imaging cap or the insertable portion. The camera may be disabled during the monitoring and inactive periods. Advantageously, enabling the camera only under predetermined conditions, including engagement, not only saves power, but also minimizes the damage that may be caused by hot-swapping the reusable and insertable portions. Table 1 summarizes a multiplicity of operating modes of the viewing instrument based upon the state of its components as described above. However, the modes described herein are exemplary, and additional or alternative criteria may be used to determine the same or more operating modes.

TABLE 1

| MODE | Camera | Display device | Control component |
| --- | --- | --- | --- |
| Active | Enabled | Enabled | Enabled |
| Sleep | Disabled | Disabled | Enabled |

TABLE 1-continued

| MODE | Camera | Display device | Control component |
| --- | --- | --- | --- |
| Monitoring | Disabled | Disabled | Enabled |
| Inactive | Disabled | Disabled | Disabled |

In another example, the visualization instrument, either or both the reusable and insertable portions, comprise a motion sensor. Exemplary motion sensors include micro-electromechanical sensors (MEMS), e.g., inertial sensors, gyroscopes, accelerometers, rate sensors, and inclinometers, configured to detect absence of motion. If absence of motion during a predetermined time period is detected, all functions except motion detection may be shut down to save power, thus placing the instrument in sleep mode. Once motion is detected during sleep mode, all functions may be re-established without performing start-up routines to quickly enable full functionality.

When the insertable portion is intended to be a single-use disposable unit, potential re-usability of the insertable portion may be of concern to practitioners, hospital administrators and others responsible for patient safety. Advantageously, in one embodiment the reusable portion may disable or not enable the insertable portion if the insertable portion has been previously used, thereby alleviating or eliminating the concern. One exemplary feature for preventing repeated uses is described herein as a single-use fuse. Generally, a single-use fuse feature detects an irreversible change to the insertable portion or the handle. Another exemplary feature is status tracking. Status tracking enables an insertion portion to be used once and then discarded, e.g. a disposable insertion portion, and also enables a permitted number of uses. If the insertable portion is intended to be used a limited number of times, such portion defined herein as "reposable." Tracking features are used to count the number of uses and to disable the reposable unit after the limit has been reached. Described below are examples of such features. Generally, in a status tracking embodiment, the insertable portion comprises an identification feature to track the number of uses. The reusable portion or the blade can be configured to detect the identification feature. The reusable portion or an associated database and processing system can track uses. In a further example, reusable blades and insertion portions can be used with multiple reusable portions so long as the use limit has not been reached. The program may indicate the status of the insertable portion or the blade with the display device. The identification information may be encrypted to prevent tampering. An anti-tampering integrated circuit may be coupled to the conductor in the insertable portion.

Additional variations of single-use fuses are described below. In one variation thereof, a tab is provided which is deformed, e.g., broken, when the insertable portion is coupled to the reusable portion or when it is disengaged. The reusable portion detects the broken tab when an attempt is made to re-use the insertable portion. For example, the housing may contain an angled protrusion which enables a tab in the proximal cavity of the handle to pass over it. When the insertable portion is disengaged, the angled protrusion tears the tab. Upon re-engagement, the reusable portion detects the deformed tab. Exemplary detectors include limit switches, optical sensors, pressure sensors, and the like. An alterable mechanical key/slot may be used as well.

In another variation thereof, a film or coating that changes color after being exposed to the environment is provided in or on the insertable portion or the blade. If the color change is irreversible, for example by an irreversible chemical reaction. UV activated cross-linking of polymers and the like, then the feature is a single-use feature. However, the feature may be a status tracking feature if the color change is reversible. Upon detection of the color change to a predetermined color, or absence of a predetermined color, software may disable the insertable portion or changes its status. The color may be detected with a detector in the housing or in the first image stream. Environmental variables include, without limitation, air, moisture, e.g. saliva, pressure, e.g. touch or heat, and other suitable variables. Sensors may be provided in the insertable portion to detect the environmental variables. For example, MEMS IC's may be provided on the external surfaces of the insertable portion. The environmental variable may have to be maintained in the changed state for a predetermined amount of time. For example, temperature may have to be greater than 75 degrees for one minute to trigger the status change.

Additional variations of status tracking features are described below. In one variation, the insertable portion is encoded by an identification component such as an electronic identifier (ID) or a unique feature detectable in the first image stream. Electronic ID features may comprise, without limitation, an RFID passive or active transmitter, a camera ID, a programmable ID located in an IC in the insertable portion, and the like. Upon engagement, the reusable portion detects the identification component, determines the status, and activates the insertable portion if the status indicates first use or reposable use less than the prescribed limit.

In another variation, the distally-facing surface of the glottis-engaging protrusion located at the distal end of the insertable portion is encoded with a pattern viewable by the image sensor. The software detects the pattern in the image stream. The pattern may comprise holographic keys molded or engraved in the distally-facing surface and may be designed to change during use so that a subsequent use may be detected.

In a further variation, the identification component comprises a physical mark in the insertable portion which is sensed by the reusable portion to determine first-use or re-use. Exemplary identification components include barcodes, luminescence marks, color keys, holographic keys, magnetic keys, and the like. Sensors adapted to sense corresponding physical marks include microbarcode readers having high magnification objectives to enable minimization of the size of the physical mark, optical sensors and/or detectors, optical sensors or detectors sensitive to holographic diffraction patterns. Hall effect sensors, pressure sensors or detectors, contact switches, and other suitable sensors. Combinations of physical marks are also envisioned, such as a key/slot combined with magnetic or optical marks. Advantageously, the identification component may also identify the type, make and model of the insertable portion, display, and/or record that information, including date and GPS stamp, to a second image stream produced for forensic use. In one example, the control component adds the forensic information to the first image stream to generate the second image stream. In another example, the forensic data is stored and transmitted separately from the image stream.

In another embodiment of the visualization instrument, fluid management lumens are provided. In one example thereof, the insertable portion includes a lumen for providing or withdrawing fluids to or from the patient. In one variation thereof, the lumen is molded opposite the guide pathway. In another variation, a plurality of small channels are included in the molded parts of the insertable portion with distal apertures located around the imaging assembly so as to not increase the size of the insertable portion. The lumen or the channels are connected to external tubes to transfer fluids, e.g. medications or bodily fluids, therethrough to and/or from an external fluid reservoir. Exemplary fluids provided to the patient include liquids, air, and gases.

In yet another embodiment of the visualization instrument, comfort features are provided. In one example thereof, a blade comprises a first material which imparts structure and rigidity to the insertable portion and a second material coupled to the first material to provide a soft and resilient feel. The second material extends, at least partially, over the surface of the handle and is textured to increase grasping comfort. In another example, sensors are placed beneath the second material to detect pressure and trigger status changes.

Figure 7:
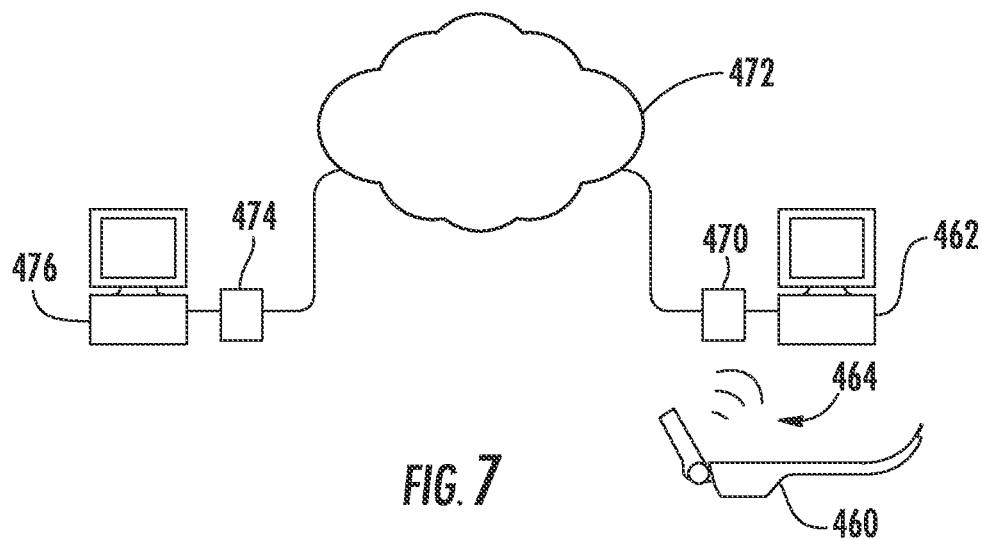
FIGS. 7 and 8 are diagrammatic views of embodiments of visualization systems.
Figure 8:
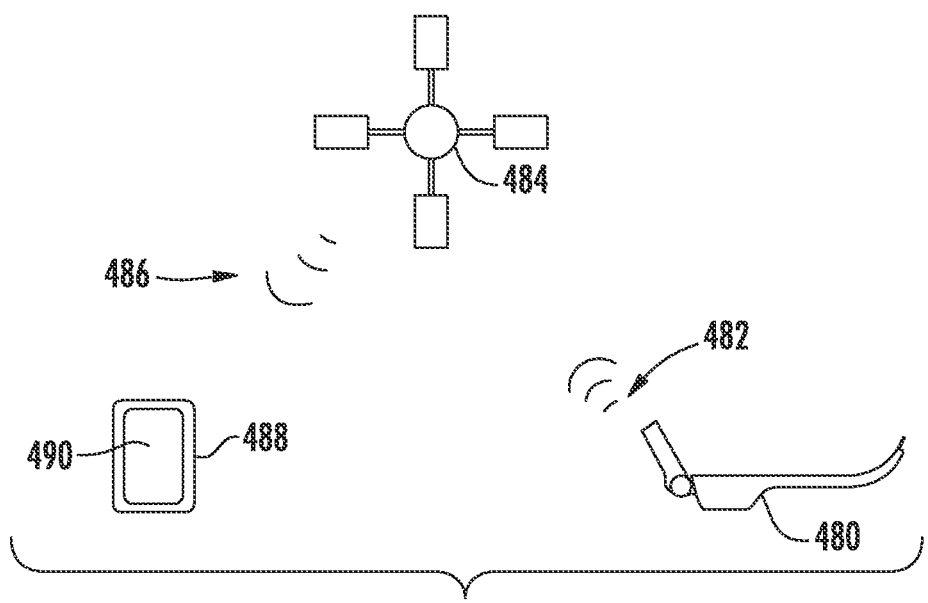

Exemplary visualization systems are described with reference to FIGS. 7 and 8. Represented therein are visualization instruments, illustratively intubation instruments 460 and 480, a local processing system, illustratively computer 462, and remote processing systems, illustratively computer 476 and portable device 488. Portable device 488 may comprise a PDA such as a BLACKBERRY™, IPOD™ and portable phone with viewable screen 490. By local and remote processing systems it is meant devices capable of performing programmed instructions accessible in a storage device such as memory, compact disk and the like. By remote processing system it is meant a processing system which is not necessary to generate images with the visualization device but which is provided to view images obtained with the visualization device. The remote processing system may be located in the same room with the visualization instrument, in a different room in the same locality, or in a different locality, e.g., in a different city. FIG. 7 illustrates a system in which a visualization device directly transmits video images electronically to computer 462. The visualization device may transmit through hardwired or wireless communication links. A wireless signal 464 is illustrated. Additionally, the communication link may comprise a physical connector. BLUETOOTH™ device, cellular modem, IR or other communication link. Computer 462 may re-transmit the video images through a modem/router 470 to the internet, represented by a cloud 472, and thereafter to a modem/router 474 and remote computer 476. In an alternative embodiment of a visualization system. FIG. 8 illustrates a visualization device transmitting video images to a communications satellite 484 for retransmission to a processing system 488. Signals 482 and 486 are cellular signals.

The systems depicted in FIGS. 7 and 8 are exemplary embodiments of more general systems. For example, signal 464 may be received by modem/router 470 without a local processing system. Analogously, intubation device 480 may transmit wirelessly to a local processing system and the local processing system may use cellular communications to reach a remote processing system. A local processing system advantageously enables use of low power wireless transmission to save the power of the intubation device. In yet another embodiment, the reusable portion transmits an image stream to a cellular phone, the cellular phone transmits the image stream to the remote computer, the remote computer receives the image stream, receives input from a remote practitioner, and transmits the same back to the cellular phone, and the cellular phone, the visualization instrument, either, or both, provides the feedback to the local practitioner. Commonly known cellular phones and PDAs comprise all the necessary elements such as displays, microphones, keyboards, and communications components to simultaneously display images and transmit text or audio signals. Advantageously, the remote two-directional link between the visualization instrument and the remote device, whether a computer, cellular phone or the like, may be used for teaching and forensic purposes in addition to providing feedback to the practitioner performing the intubation.

Remote feedback enables a practitioner observing remotely to provide suggestions and other information to the local practitioner. For example, a medical technician may perform the intubation in a battlefield or accident scene as directed by a physician at a hospital. The remote feedback may be text, image, audio or any other type of feedback. Visual feedback may be provided in the display device through the electronic communication link between the visualization device and the local computer. The local computer or the reusable portion may also include speakers to aurally communicate the remote feedback to the practitioner. In one example of the present embodiment, the reusable portion or the local computer provides feedback to the practitioner, the source of the feedback being generated with the remote processing system. Images generated with visualization device may be viewed by a practitioner in the display device of the reusable portion, and in the local and remote processing systems simultaneously. The images displayed by each device may be the same or different. Local computer 462 may incorporate display features suitable to local use while remote computer 476 or portable device 488 may incorporate features suitable for remote use or compatible with their processing capabilities.

Figure 9:
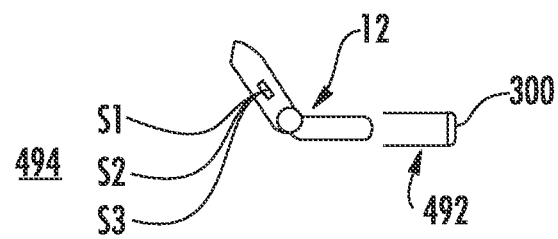
FIG. 9 is a depiction of a visualization device operable with the visualization systems of FIGS. 7 and 8.

In another example, the communication systems depicted in FIGS. 7 and 8 are leveraged with the addition of another component of a visualization system, illustratively imaging cap 492, comprising imaging assembly 100, illustrated in FIG. 9. In the field, a medical technician may carry reusable portion 12, a blade and imaging cap 492. After intubating the patient, the medical technician may remove the blade and replace it with imaging cap 492 with which he/she can then scan the patient to enable remote viewing of the patient's wounds. A multisensor adapter is also provided, illustratively multisensory adapter 494 having sensors S1, S2 and S3, which may be connected to a port of reusable portion 12 or a communications port provided in imaging cap 492. Sensors S1, S2 and 83 may comprise, for example, a temperature sensor, a blood pressure sensor, and a cardiac rhythm sensor. Either reusable portion 12 or imaging cap 492 may comprise processing capabilities to sample sensor signals which are then transmitted to the local or remote processing system. Of course, the sensor signals may also be processed by the reusable portion 12 which then display indications corresponding to the sensor signals such as blood pressure alarms and the like.

In a further example of a visualization system, the local computer collects patient information and transmits the information to the reusable portion. The reusable portion displays on-screen indicators in the display device to alert the practitioner without requiring the practitioner to look away to receive the same information. On-screen information may include vital signs. $CO_2$ levels in the air exhaled by the patient, temperature, oxygen saturation, pulse, blood pressure and any other patient vital signs. On-screen information may also include corresponding indicators such as alarms, color-coded thresholds indicating that the vital signs are approaching concerning levels, and alarms/indicators corresponding to the performance of equipment such as ventilators. In one variation thereof, the reusable portion displays on-screen information and indicators generated by the reusable portion. Such information may include parameters extracted from the first image stream, indicators from comparisons of landmarks in the first image stream to the expected location of the landmarks relative to the insertable portion, and other data which the reusable portion may collect with sensors such as those attached to the communications port.

The visualization system is well suited for emergency, rescue and military operations. In a further embodiment of the visualization system, communications gear typically used in such operations are provided with a cradle in which the reusable portion is stored. The cradle comprises a charging housing to re-charge batteries in the reusable portion. The cradle may comprise UV lights to sterilize the reusable portion, since the reusable portion may be used several times before the rescue team or military unit returns to base. Due to the availability of power and telecommunications gear, the reusable portion can be designed to communicate locally only and thereby its size and weight may be minimized. The cradle may also sterilize a reposable portion. Of course, the use of such cradles is not limited to rescue and military operations. Cradles may be used in any environment in which the reusable portion can be used.

Figure 14:
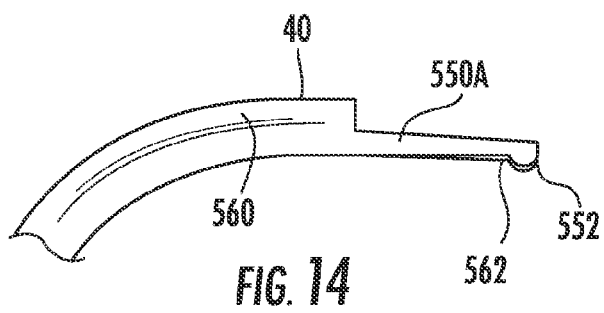
Figure 15:
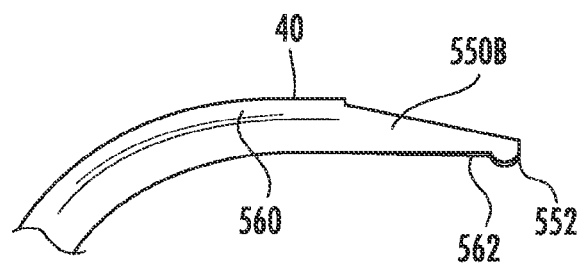

Another embodiment of a visualization instrument is described below with reference to FIGS. 10 and 11 wherein views of an intubation instrument denoted by the numeral 500 are described. Intubation instrument 500 comprises reusable portion 12 having a display device 110 pivotably coupled via a hinge 22 to a housing 108 and a blade 514 having a handle 30 in a proximal end spaced apart from a distal end having distal cavity 568 in which imaging assembly 100 is located. Blade 514 comprises a passageway 536 which is designed to guide insertion of a catheter into the larynx of a patient. Passageway 536 is defined by interior surface 542 of a medial wall 44 and interior surface 538 of an anterior wall 534. Blade 514 further comprises an atraumatic distal tip 546 having a surface 570 and a protrusion 552 disposed across its distal edge 554 (shown in FIGS. 12 and 13). By atraumatic it is meant a feature without surfaces generally known to cause trauma such as sharp edges and tightly radiused protrusions. Edges 556 and 558 are angled so that distal edge 554 is narrower than the width of the insertable portion. Of course, the width of the insertable portion can equal the width of distal edge 554 in which case edges 556 and 558 will coextend with walls 534 and 560. Surface 570 may comprise any smooth surface or any textured surface such as any one of surfaces 700, 710, 730 or 740 (shown in FIGS. 20-23). Atraumatic wall portion 550 is also included to reduce the sensory effect caused by blade 514 as it is moved laterally to displace the tongue of the patient. Wall portion 550 partially extends wall 560 along the edge of distal tip 546. Medial wall 44 defines one side of the distal cavity. On the opposite side, a distal cavity wall may extend past the end of the distal cavity towards and until it reaches distal tip 546. The portion of the wall opposite medial wall 44 which extends beyond the opening of the distal cavity is denoted by numeral 550. Wall portion 550 may extend from posterior surface 40 or any point intermediate posterior surface 40 and interior wall 538 as shown in FIGS. 14 and 15 (see wall portions 550A and 550B). Distal tip 546 may include the protrusion denoted by numeral 552 which is provided to reduce trauma.

In a further embodiment of an intubation instrument, passageway 536 is partially constrained at the distal end of the insertable portion by an extension portion of a posterior wall such that an internal surface of the extension portion of the posterior wall faces interior surface 538. The extension portion may be provided integrally with the posterior wall, for example as a single extruded part, or may be attached to the insertable, portion, for example by providing a layer that can be adhesively bonded to surface 40 of the posterior wall. The extension portion may comprise an elastomeric composition, as described above, which resiliently allows removal of the insertable portion after an endotracheal tube is inserted through the passageway into the larynx of the patient. The extension portion, medial wall 44, and anterior wall 38 form a C-channel coextensive with the distal portion of passageway 536.

Figure 10:
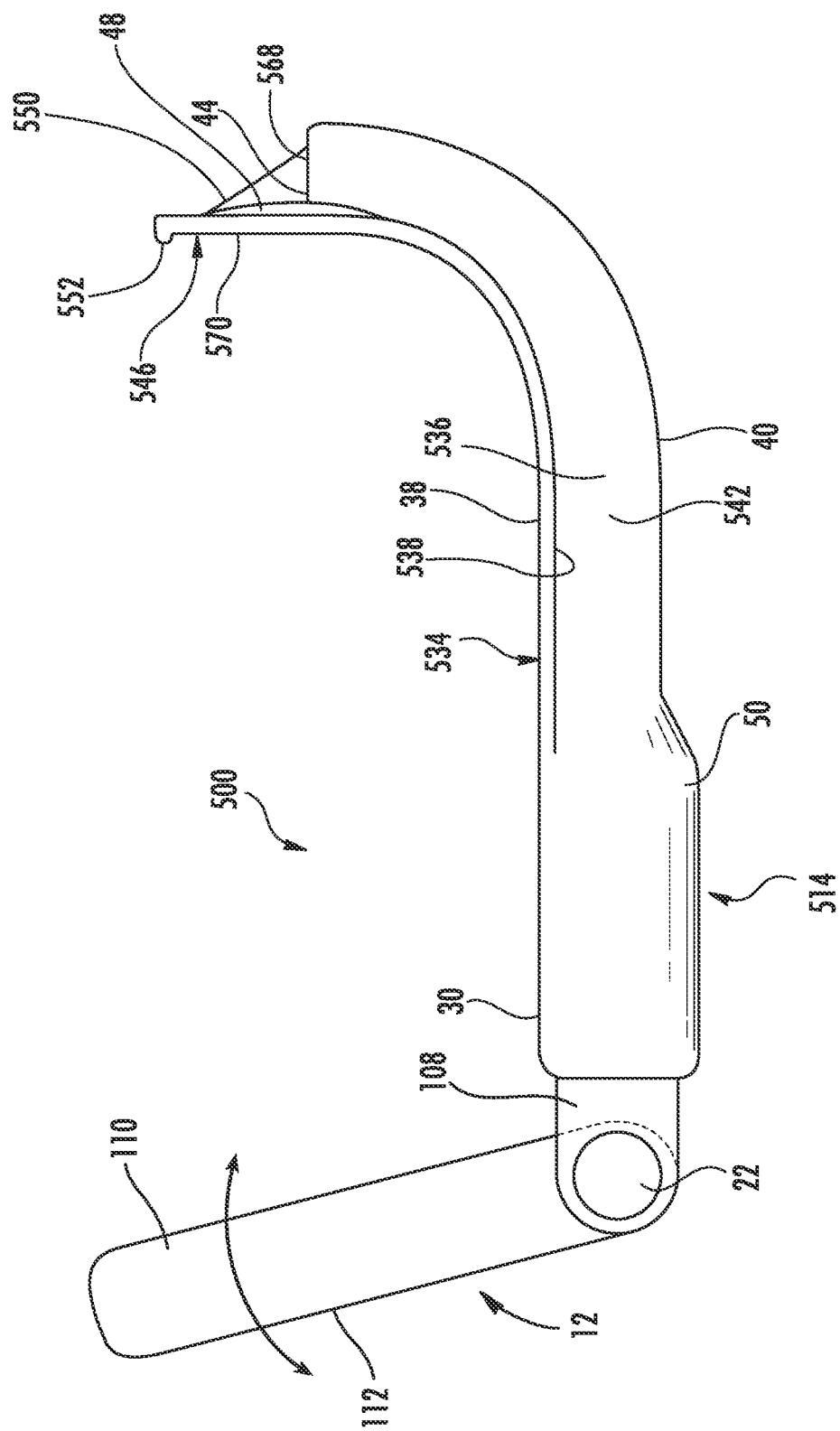
FIG. 10 is a plan view of another embodiment of a visualization instrument.
Figure 11:
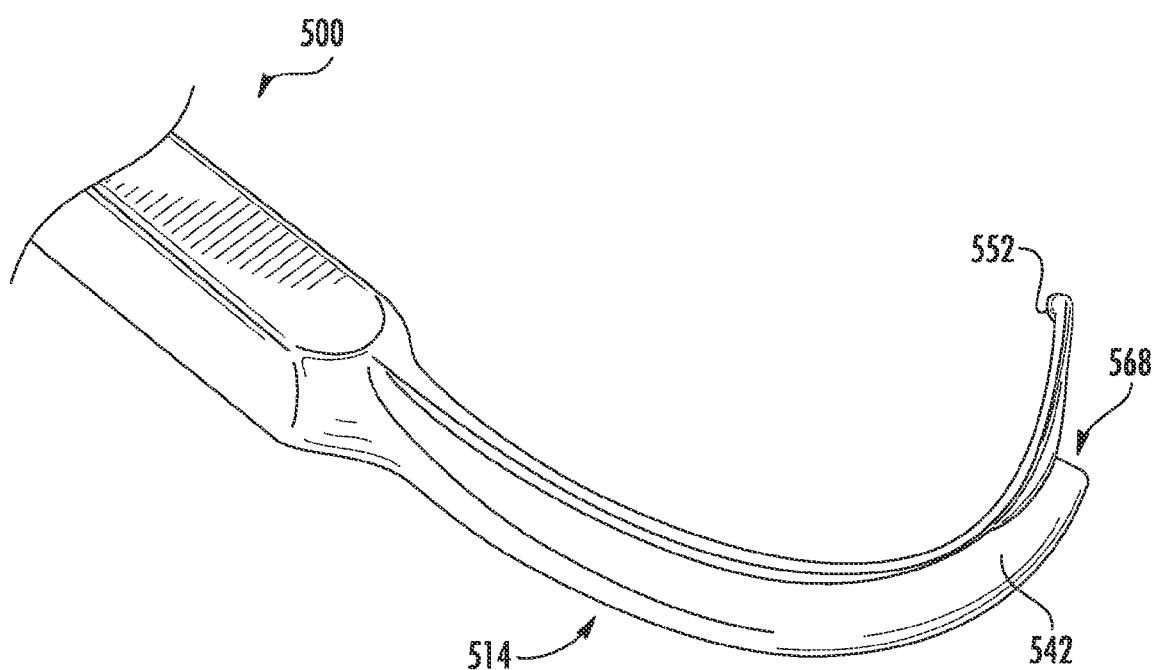
FIG. 11 is a partial perspective view of the distal portion of a blade.
Figure 12:
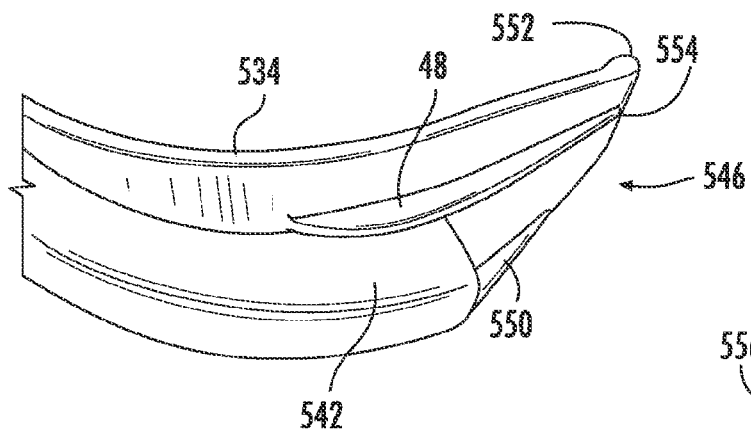
FIGS. 12 to 15 are partial views of alternative embodiments of the distal end of an insertable portion of a visualization instrument.
Figure 13:
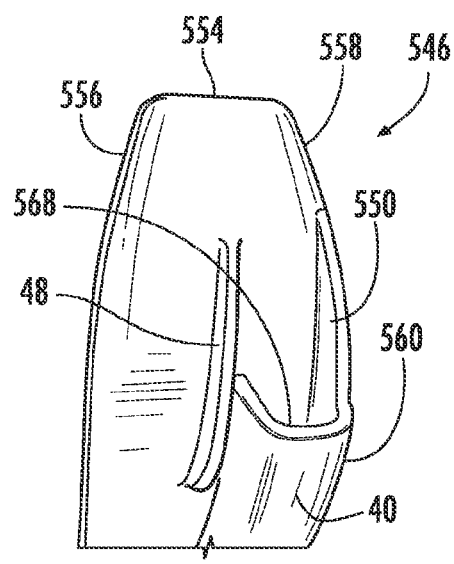

FIGS. 12-15 illustrate various adaptations of distal tip 546 having surface 570 (shown in FIG. 10). Surface 570 is substantially flat. On the longitudinal borders, next to edges 556 and 558, the surface is concave to increase the flexural strength of distal tip 546. In one example, the lateral borders of surface 570 are curved sufficiently to increase flexural strength by about 10%. Flexural strength is further increased by the addition of ridge 48. Flexural strength means the ability of the distal tip to withstand a force applied to surface 570 without bending. Flexural strength is desirable to resist the force applied by the patient's glottis as the instrument is used to displace the glottis. Of course, the actual amount of curvature needed to achieve a desired flexural strength is dependent on the thickness of distal tip 546 and its composition. In another example, shown in FIG. 18, the lateral edges of distal tip 546, denoted by numerals 556 and 558, are angled with respect to the center line of blade 514 so as to reduce the possibility of causing a traumatic experience for the patient. The angles are sufficient to reduce the length of edge 554 to the width of an average glottis of an average patient. The width of edge 554 may be wider in the case of devices made for use with adult patients and narrower for devices made for use with infants. Wall portions 550A and 550B in FIGS. 14 and 15 show that the wall height may vary to form a shallow or steep angle with reference to surface 40. In a further example, similar to the embodiment shown in FIG. 10, wall 550 reaches surface 40 thereby minimizing any edge effects which the patient might detect. The height of walls 550, 550A and 550B is a result of a compromise between the desire to reduce trauma, increase flexural strength and increase the field of view of insertable portion 514.

A number of configurations are described herein which may be provided to facilitate removal of the intubation tube. FIGS. 16 and 17 are elevation and plan views of an exemplary blade, denoted by numeral 600. Blade 600 is similar to blade 514 except that the anterior wall of passageway 36 comprises wall portions 604 and 610 rather than a continuous wall 34. Wall portions 602 and 54 comprise the lateral wall of passageway 36. Distal cavity 101 is shown opposite passageway 36. Similarly, FIGS. 18 and 19 are elevation and plan views of another exemplary blade, denoted by numeral 640, comprising an anterior wall including wall portion 654 rather than a continuous wall 34. Wall portions 644 and 54 comprise the lateral wall of passageway 36.

In an alternative embodiment, a resilient tab is positioned in the interior surface of the posterior wall and/or on the interior surface of the lateral wall, at the distal end of the insertion portion. The resilient tab is designed to push the endotracheal tube passing through passageway 36 towards distal tip 46 regardless of the tube diameter. Thus, even when the tube diameter is substantially smaller than the cross-sectional area of the passageway, the tab(s) push(es) the endotracheal tube into the proper position for insertion through the vocal cords.

Figure 20:
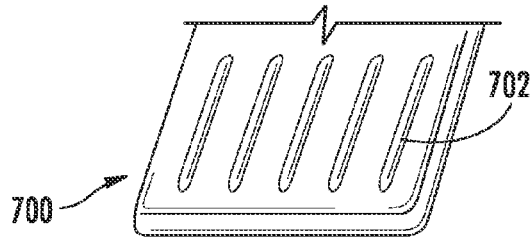
FIGS. 20 to 23 are perspective views of embodiments of distal tip surfaces.
Figure 21:
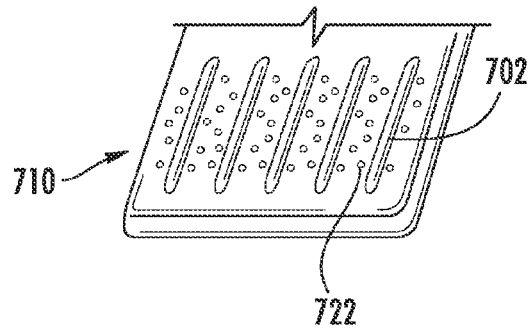
Figure 22:
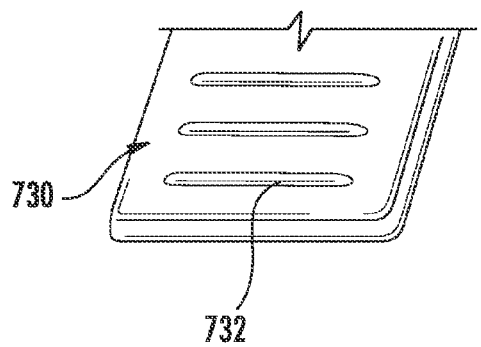
Figure 23:
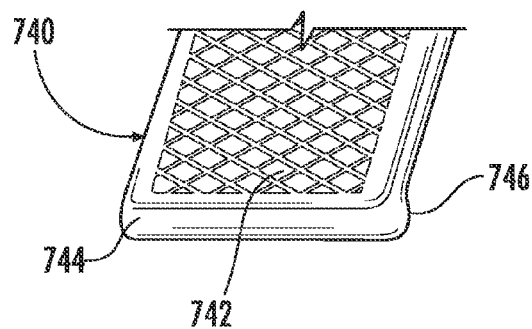

FIGS. 20-23 illustrate exemplary distal tips 700, 710, 730 and 740 exhibiting textured surfaces. The textured surfaces, and any variation thereof, may be applied to any of the anterior surfaces disclosed herein including surfaces 70 and 570. Textured surfaces may exhibit a regulated pattern, as shown in FIGS. 20-23, and may exhibit an unregulated, or random, pattern. The regulated pattern may be longitudinally aligned, as exemplified by FIG. 20, or transversely aligned, as exemplified by FIG. 22. Exemplary textured surfaces include roughness, bumps, ridges, protrusions or irregularities which have sufficiently pronounced three-dimensional characteristics so as to be visible without the aid of optical devices and to be distinguishable by touch. Since smooth surfaces are plainly known as surfaces free from roughness, bumps, ridges or irregularities, textured surfaces are by definition unsmooth even though the tactile impression they produce is not necessarily unpleasant or traumatic. FIG. 20 depicts distal tip 700 comprising a plurality of elongate ridges, illustratively ridges 702, protruding therefrom. Ridges 702 provided distal tip 700 with a surface that has two coefficients of friction depending on the measurement direction. In the longitudinal direction, the coefficient of friction may be lower than the coefficient of friction measured in a direction perpendicular to ridges 702. Advantageously, two coefficients of friction may facilitate motion in the longitudinal direction of distal tip 700 against the patient's glottis and prevent lateral motion or displacement of the glottis. FIG. 21 is similarly designed and depicts distal tip 710 comprising a plurality of protrusions 722 designed to calibrate the tension between ridges 702 and the glottis when the tip pushes against the glottis. Ridges 702 and protrusions 722 may be sized and configured to produce a desired sensation in the patient. The height, shape, and cross-sectional area of protrusions 722, as well as the separation between contiguous protrusions, may be varied. As with distal tip 700, two coefficients of friction may be obtained and protrusions 722 may be utilized to control the difference between them. FIG. 22 depicts distal tip 730 comprising a plurality of elongate ridges 732 protruding therefrom disposed perpendicularly to wall 44 The ridges are configured to prevent longitudinal displacement of the glottis after distal tip 730 contacts the glottis. Protrusions may be provided between the ridges similarly as those provided in FIG. 21. Advantageously, the ridges may enable displacement of the glottis with application of less force than would be required if the ridges were not present. FIG. 23 depicts distal tip 740 comprising a regulated pattern exemplified by pattern 742 comprising a multitude of four-sided protrusions which may provide the benefits disclosed hereinabove with respect to contact with a patient's glottis. In a variation thereof, a crisscross pattern of ridges defines four-sided cavities. The angles between the sides, and the lengths of the sides, of the four-sided protrusions or cavities, as the case might be, are varied to form at least one of squares, rectangles and diamonds. In a further variation thereof, the protrusions or cavities are oval or round. Also shown is distal protrusion 746 providing an atraumatic edge, illustratively edge 744, thereto. The atraumatic protrusion is also shown in FIGS. 10 to 11 as protrusion 552.

Figure 24:
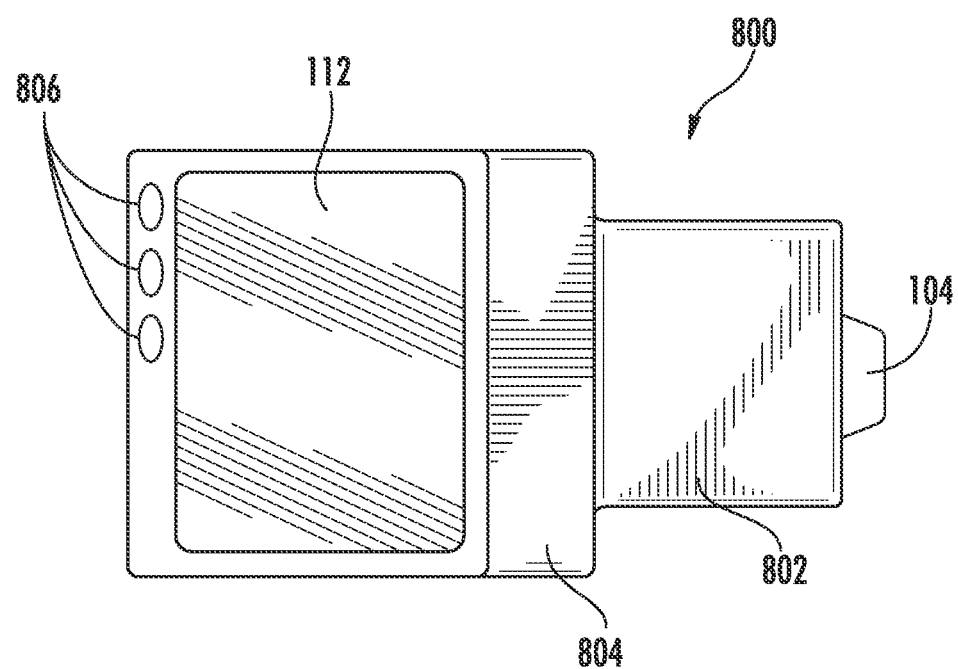
FIGS. 24 and 25 are elevation and plan views of an embodiment of a reusable portion of a visualization instrument.
Figure 25:
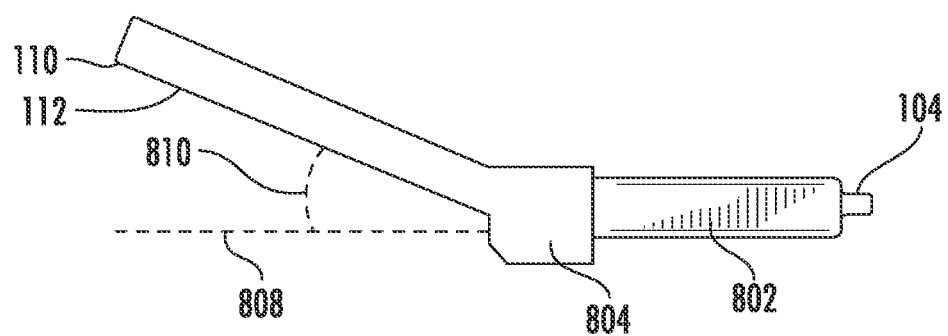
Figure 26:
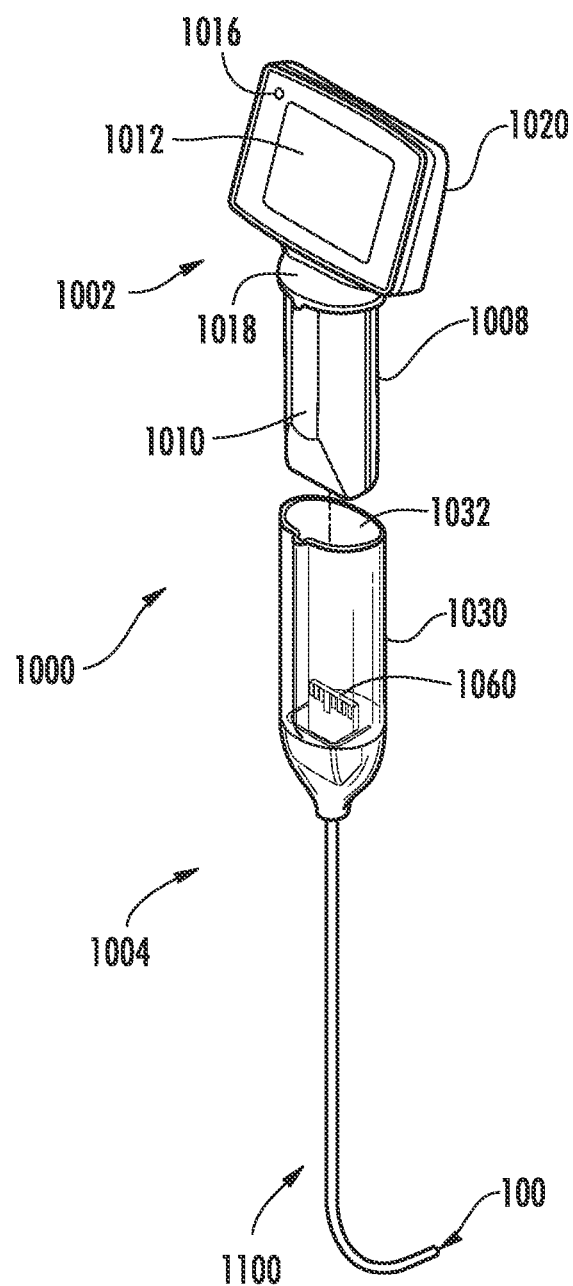
FIGS. 26 to 33 illustrate embodiments of a visualization instrument comprising a stylet.

FIGS. 24 and 25 illustrate an embodiment of a reusable portion, denoted by numeral 800, with a display device provided at a fixed angle. Reusable portion 800 comprises a housing 802 and a neck 804 coupling housing 802 to viewable screen 112. A plurality of push-buttons 806 is provided to control the intubation instrument. Exemplary push-buttons are provided to activate the camera, change display characteristics and wirelessly transmit an image stream or other data to an external device. Line 808 depicts a plane parallel to housing 802 and line 810 depicts the fixed angle at which viewable screen 112 is oriented relative to line 808. In most intubations, the practitioner stands proximally to the head of the patient facing towards the patient's feet. As the intubation device is inserted into the patient, viewable screen 112 faces the practitioner so that the practitioner may look at the display and into the oral cavity of the patient by merely shifting his/her gaze.

FIGS. 26 to 33 illustrate a further embodiment of a visualization instrument, depicted by numeral 1000, comprising a reusable portion 1002 and a stylet 1004. Reusable portion 1002 includes a housing 1008 coupled to a display device 1020 having a viewable screen 1012. Display device 1020 is supported by a support portion 1018. Display device 1020 also includes an illumination device, illustratively LED 1016, suitable for indicating a power-on status or other suitable indications such as alarms. In one example, LED 1016 blinks or flashes to indicate a condition which benefits persons not able to distinguish LED colors. Exemplary conditions include power-on, disablement due to uses exceeding a permitted number of uses, low battery, and other suitable conditions. A power-on button (not shown) may be provided in the side of display device 1020 opposite viewable screen 1012. The power-on button may be covered with resilient material (disclosed in detail further below with reference to FIGS. 40 and 41), e.g. elastomeric polymer or rubber, to seal the power-on button and enhance the ability to clean the reusable portion. Stylet 1004 comprises a handle 1030 defining cavity 1032 configured to receive reusable portion 1002 and stylet arm 1100 which supports imaging assembly 100. In one variation thereof, a silicone gasket comprising magnetic particles, and a magnetically attractive material, e.g. iron or another gasket with magnetic particles, are provided on body portion 1008 and support portion 1018, for example at the joint between body portion 1008 and neck portion 1018, to latch the insertable portion. The magnetic coupling may also form a magnetic interlock circuit which the processor of the reusable portion checks to verify proper insertion of the housing into the insertable portion or imaging cap before enabling use of the camera. In another variation thereof, one of the reusable portion and the insertable portion comprises a mechanical locking feature, e.g. a tab, which makes an audible sound when the two portions are mated together.

Figure 27:
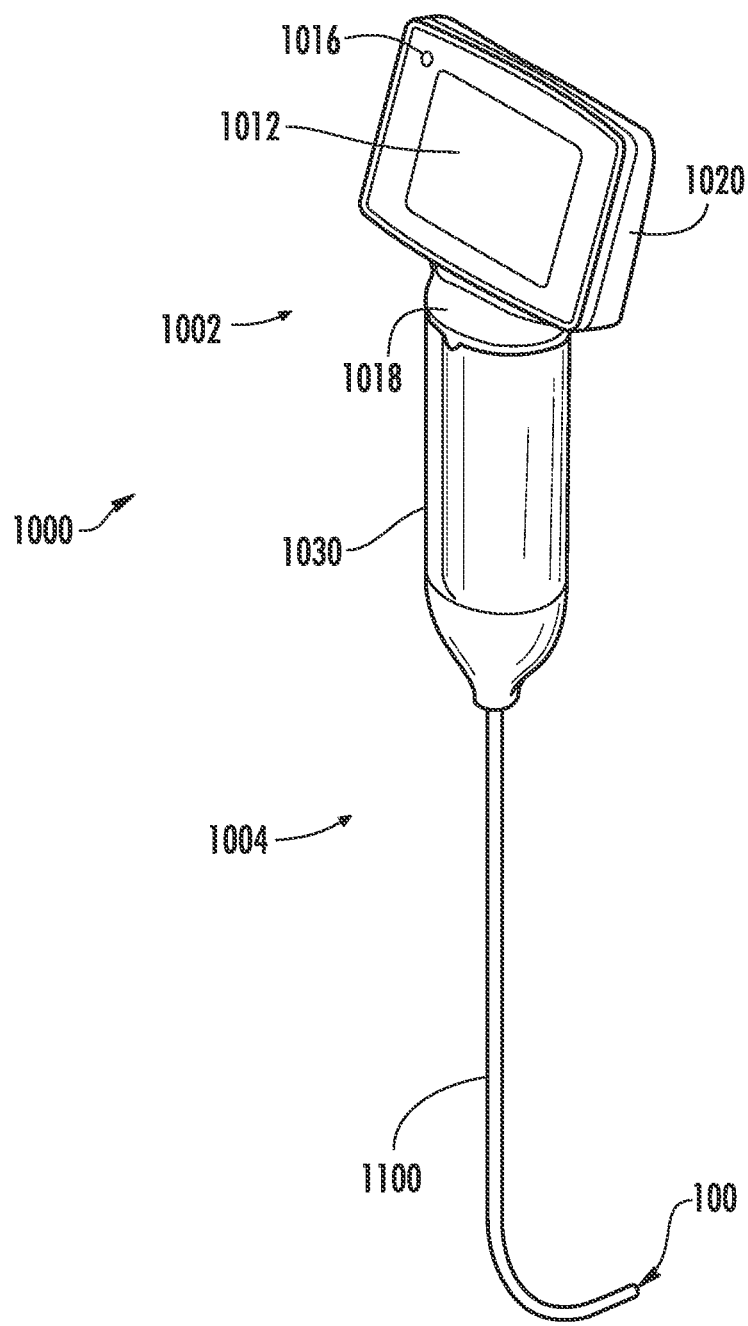
Figure 28:
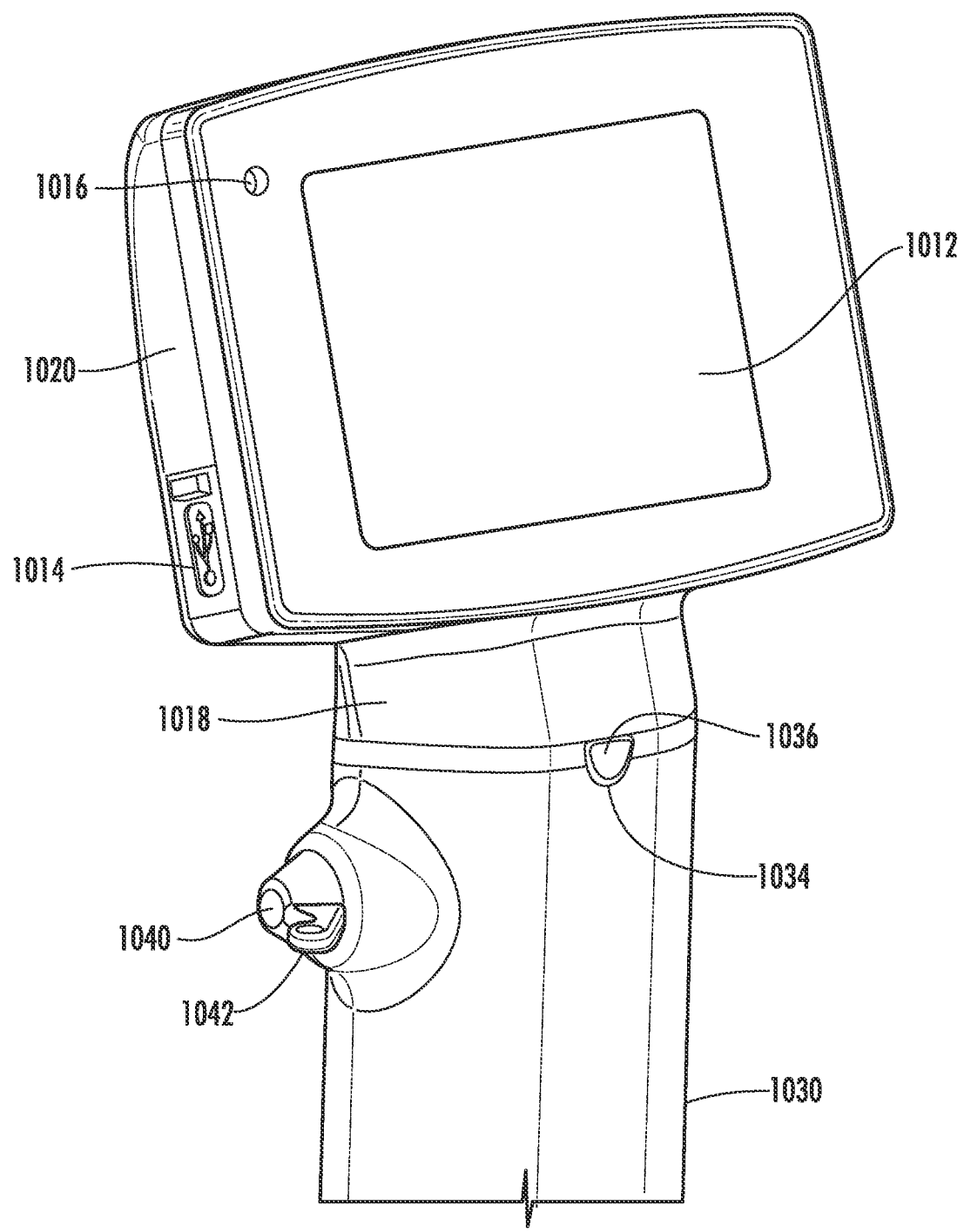

Handle 1030 may comprise a textured external surface to enhance grip. Handle 1030 includes connector 1060 adapted to communicatively couple the camera to body portion 1008. A similar connector may be provided in a cradle to charge the reusable portion when not in use. Alternatively, or additionally, a cradle may comprise an inductive charger and either of the reusable portion or the insertable portion may comprise a matching induction coil. When the intubation instrument is placed in the cradle, the inductive charger charges the induction coil to recharge the intubation instrument. A least a portion of a wall of handle 1030 may be sufficiently thin to enable the electromagnetic waves emitted by the inductive charger to efficiently pass through the wall. FIG. 27 illustrates reusable portion 1002 inserted into cavity 1032. FIG. 28 illustrates features of display device 1020 such as a communication port cover 1014 underneath which is a communication port and a protrusion 1036 provided as a positive interface feature to indicate the proper orientation of display device 1020 relative to handle 1030. Exemplary communication port receptacles include USB, mini-USB, micro-USB, serial, co-axial, IEEE 1994 format, and any other known connector for any communication standard. Protrusion 1036 matches a notch 1034 located in handle 1030. As disclosed in more detail with reference to FIGS. 43 and 44, in one embodiment of a visualization instrument, the visualization instrument comprises audible engagement features. In one example thereof, protrusion 1036 makes an audible sound when it engages notch 1034 to indicate to a user that handle 1030 and display device 1020 have been properly engaged.

Figure 29:
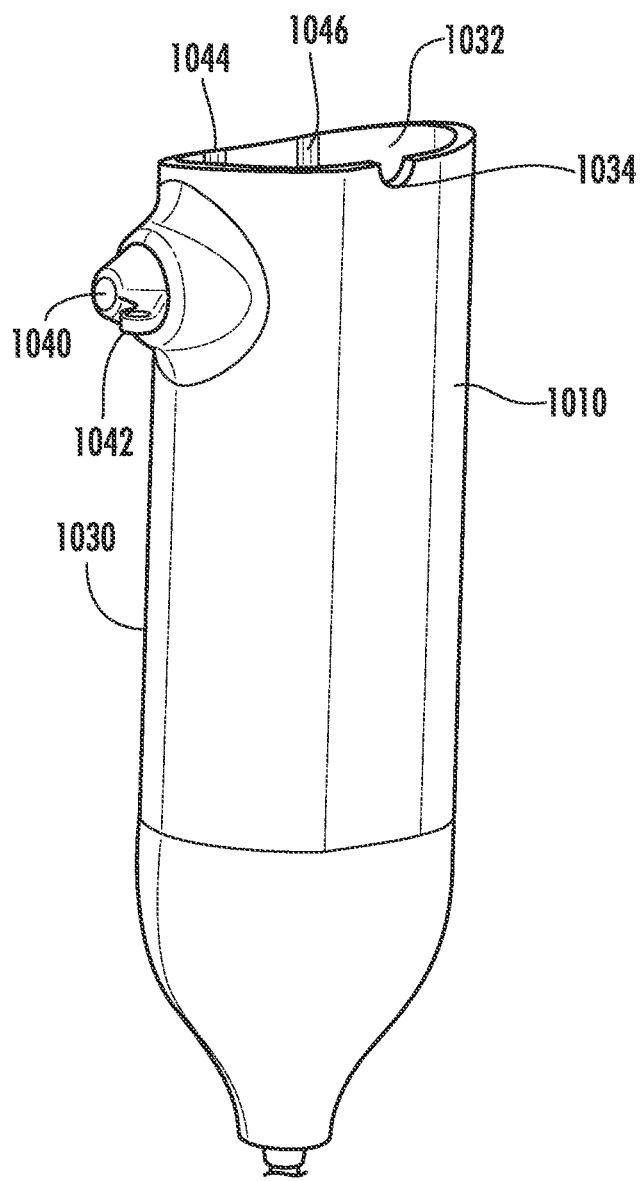
Figure 30:
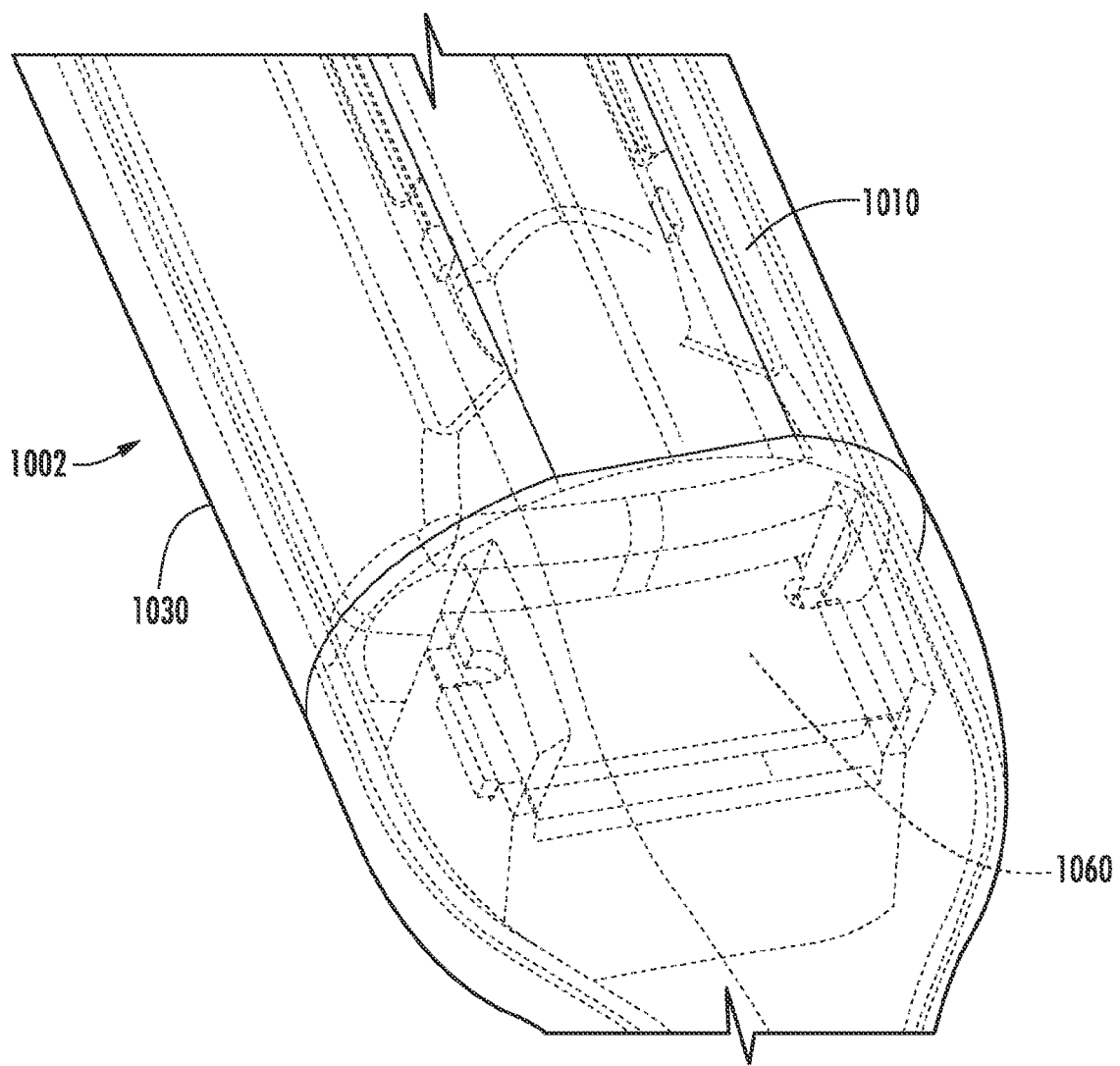

FIGS. 29 and 30 illustrate additional features of handle 1030. In one example, alignment features are provided, illustratively guide channels 1044 and 1046, in the interior surface of the anterior wall of handle 1030 to receive elongate longitudinal rails located in the anterior surface of body portion 1008 and to ensure proper coupling between reusable portion 1002 and handle 1030. Any of a variety of other mechanical keying features may be employed. In another example, the posterior surface of handle 1030 is substantially flat and the anterior surface of handle 1030 (one of which comprises compartment cover 1010) is substantially round or oval to assist the user in determining by touch the orientation of reusable portion 1002 relative to handle 1030. Handle 1030 may be manufactured as two or more injection molded parts which snap together. An optional rotary effector and lever are shown, illustratively rotary thumb switch 1040 and lever 1042, and their functions are described further below with reference to FIG. 32. FIG. 30 illustrates in phantom the location of a connector 1060. Connector 1060 fits into an interface slot (not shown) in reusable portion 1002 which receives connector 1060 to communicatively couple body portion 1008 to handle 1030.

Figure 31:
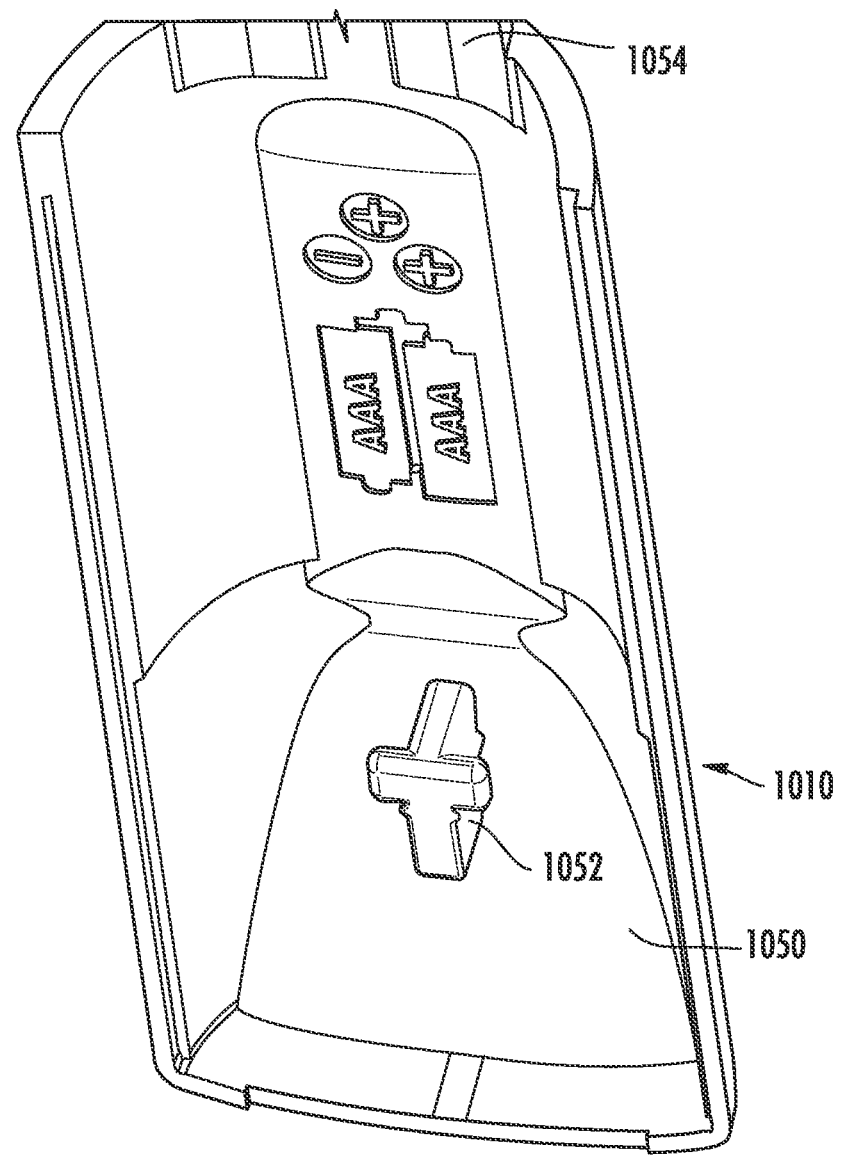

FIG. 31 illustrates the internal side of compartment cover 1010. In use, compartment cover 1010 is positioned to cover an internal compartment, e.g. battery compartment. It has an internal distal surface 1050 connected to a surface 1054. A key latch structure 1052 extends from internal surface 1050 and mates with a mirror image structure provided in body portion 1008 when compartment cover 1010 is secured over the compartment, thereby positively locking compartment cover 1010 in place.

Figure 32:
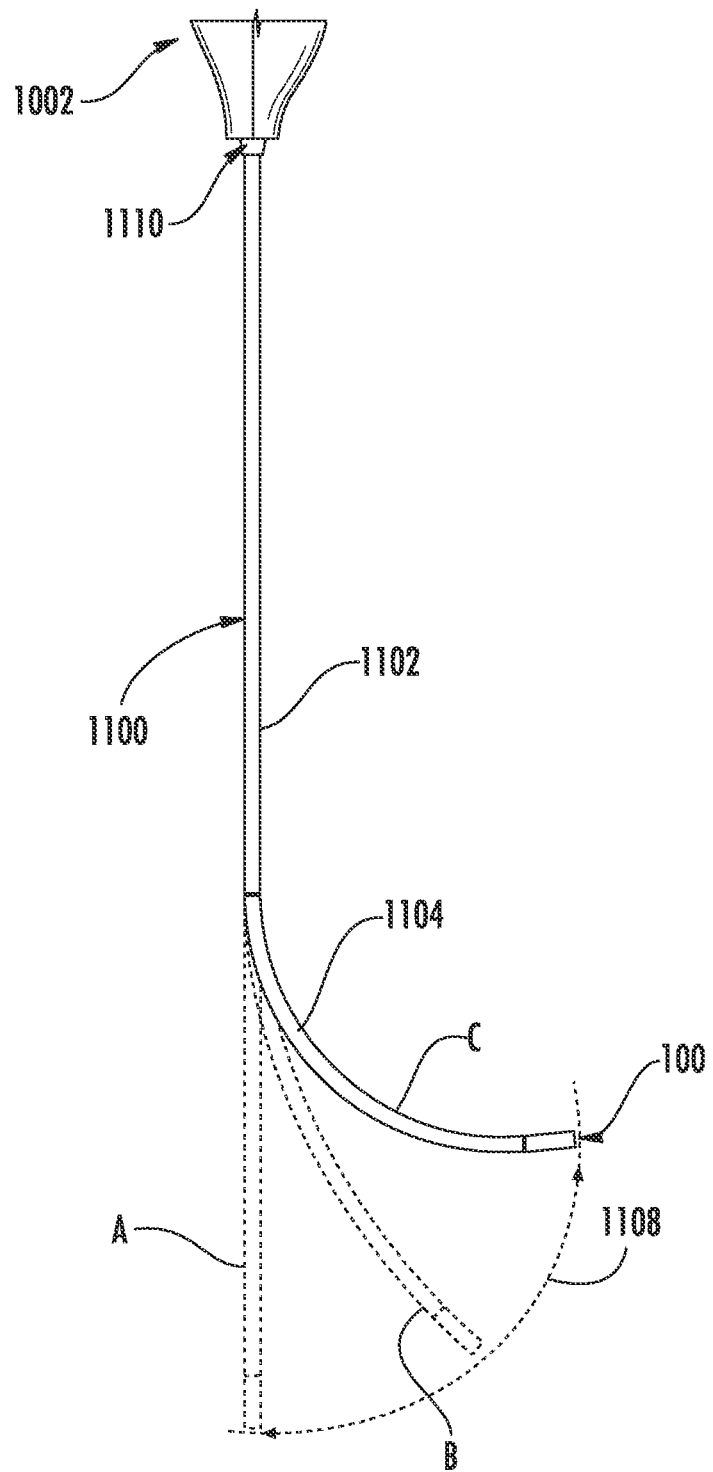

In one example of the present embodiment, stylet 1004 is steerable. FIG. 32 illustrates a variation of a steerable stylet comprising stylet arm 1100 having a shaft 1102 at its proximal end and a flexible shaft 1104 at its distal end. Flexible shaft 1104 may bend relative to shaft 1102 producing a plurality of viewing positions, illustratively positions A, B, and C which are steerable in an arc, illustratively arc 1108. Although a one-dimensional arc is shown, the arc may be formed in any orientation. Consequently, the tip of flexible shaft 1104 is repositionable with three degrees of freedom. Assigning the longitudinal axis of shaft 1102 to be the Z-axis, the tip of flexible shaft 1104 may be rotated anywhere in the X-Y plane. A steering mechanism is provided in stylet handle 1030 and shaft 1102 (not shown) to bend shaft 1104. An exemplary steering mechanism is a gear train or guide wire. The gear train is activated by a rotary thumb switch 1040, comprising a lever 1042, which is provided to enable a user to easily actuate rotary thumb switch 1040 to cause stylet arm 1100 to change the position of its distal end and thereby to change the viewing angle of the camera.

Figure 33:
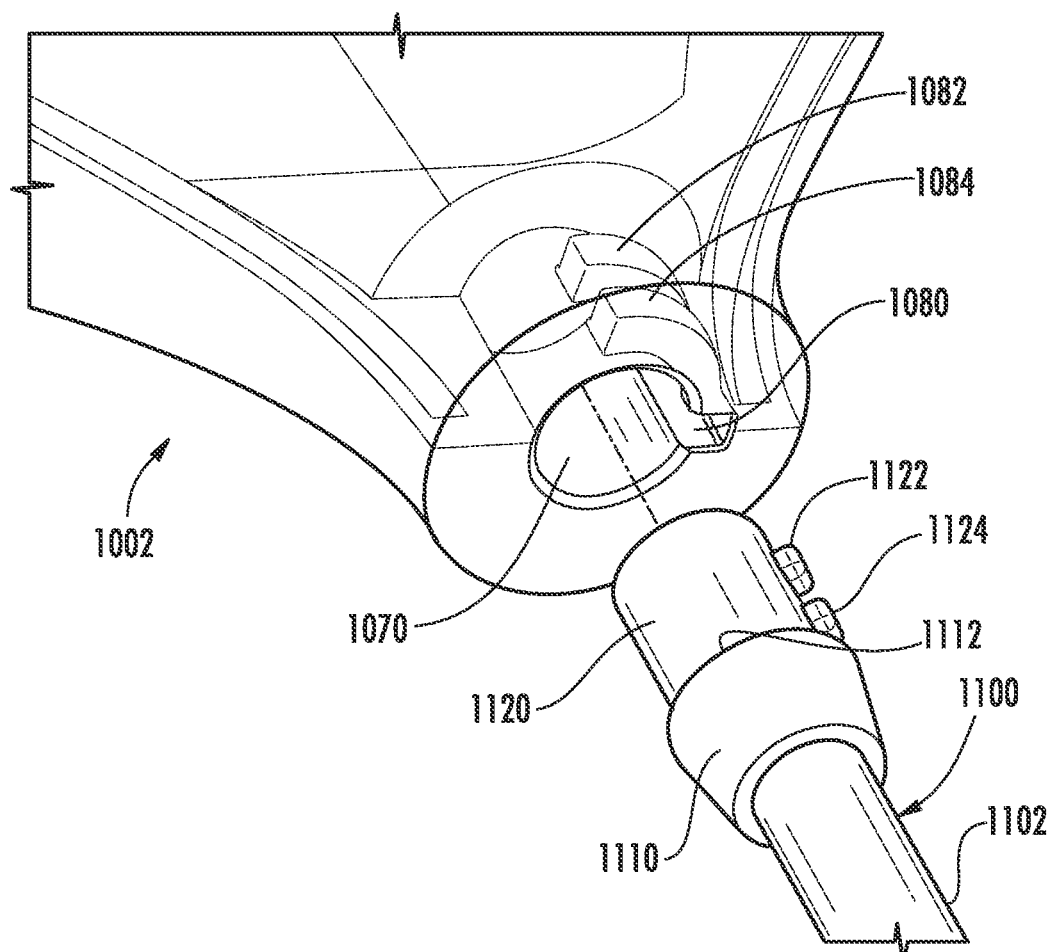

Stylet arm 1100 may be permanently or removably attached to stylet handle 1030. FIG. 33 illustrates an example of a removably attachable stylet arm 1100. An aperture 1070 is provided in stylet handle 1030 to receive a stylet arm connector 1120 having protrusions 1122 and 1124 thereon extending radially outwardly from its surface. Aperture 1070 comprises a longitudinal round aperture, a longitudinally extending slot 1080 provided to receive protrusions 1122 and 1124, and radial slots 1082 and 1084. Stylet arm 1102 further comprises a collar 1110 having a shoulder 1112. Stylet arm connector 1120 penetrates aperture 1070 when protrusions 1122 and 1124 are aligned with slot 1080. When shoulder 1112 engages stylet handle 1030, protrusions 1122 and 1124 are aligned with radial slots 1082 and 1084, respectively. Stylet arm 1100 may then be rotated counter-clockwise to lock stylet arm 1100 with stylet handle 1030 when protrusions 1122 and 1124 enter slots 1082 and 1084. In a further example, a removable sheath envelops the stylet. After use, the stylet sheath is discarded. A new sheath is placed over the stylet to reuse the stylet.

Figure 34:
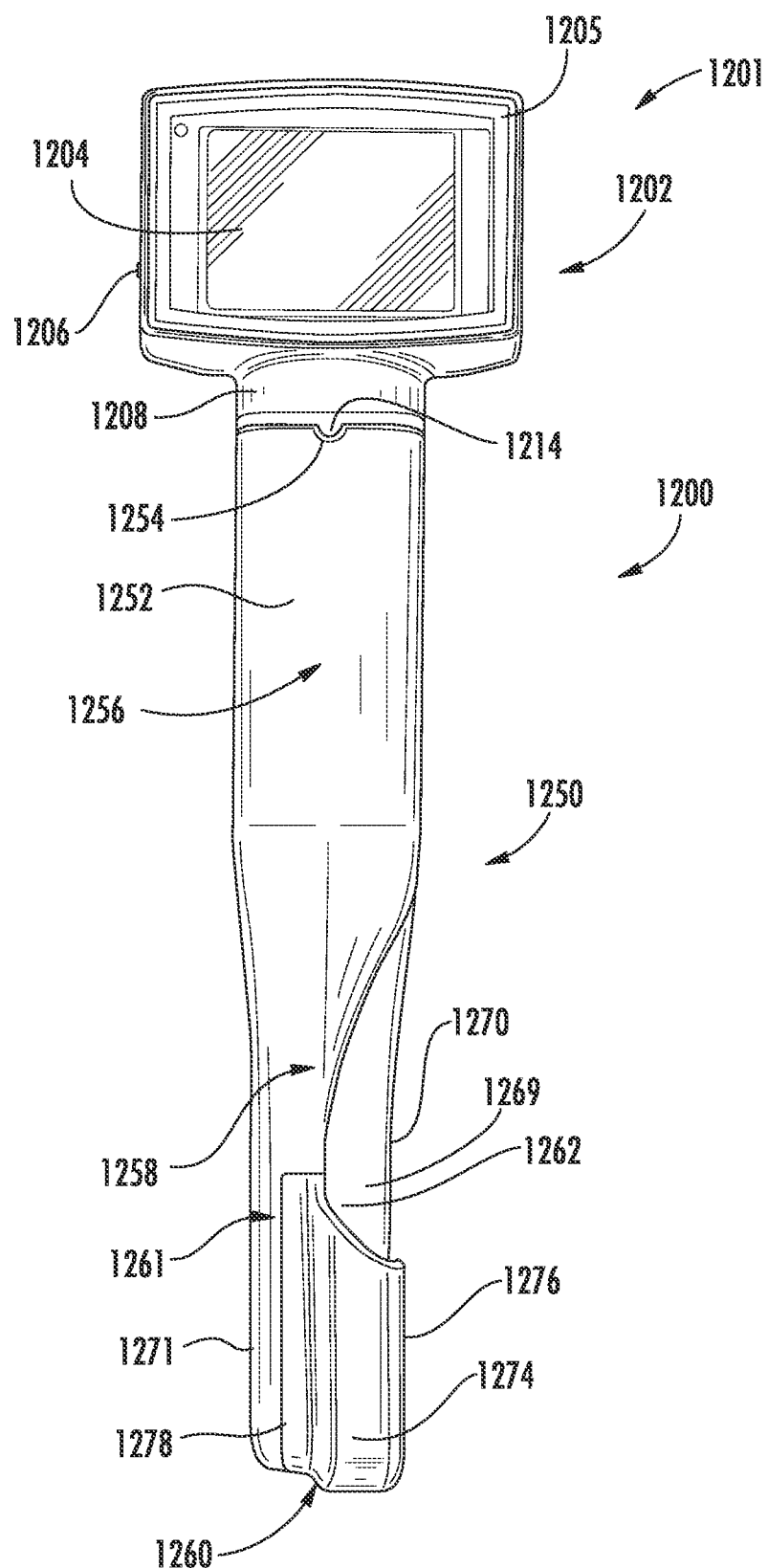
FIGS. 34 and 35 are plan and perspective views of another embodiment of a visualization instrument.
Figure 35:
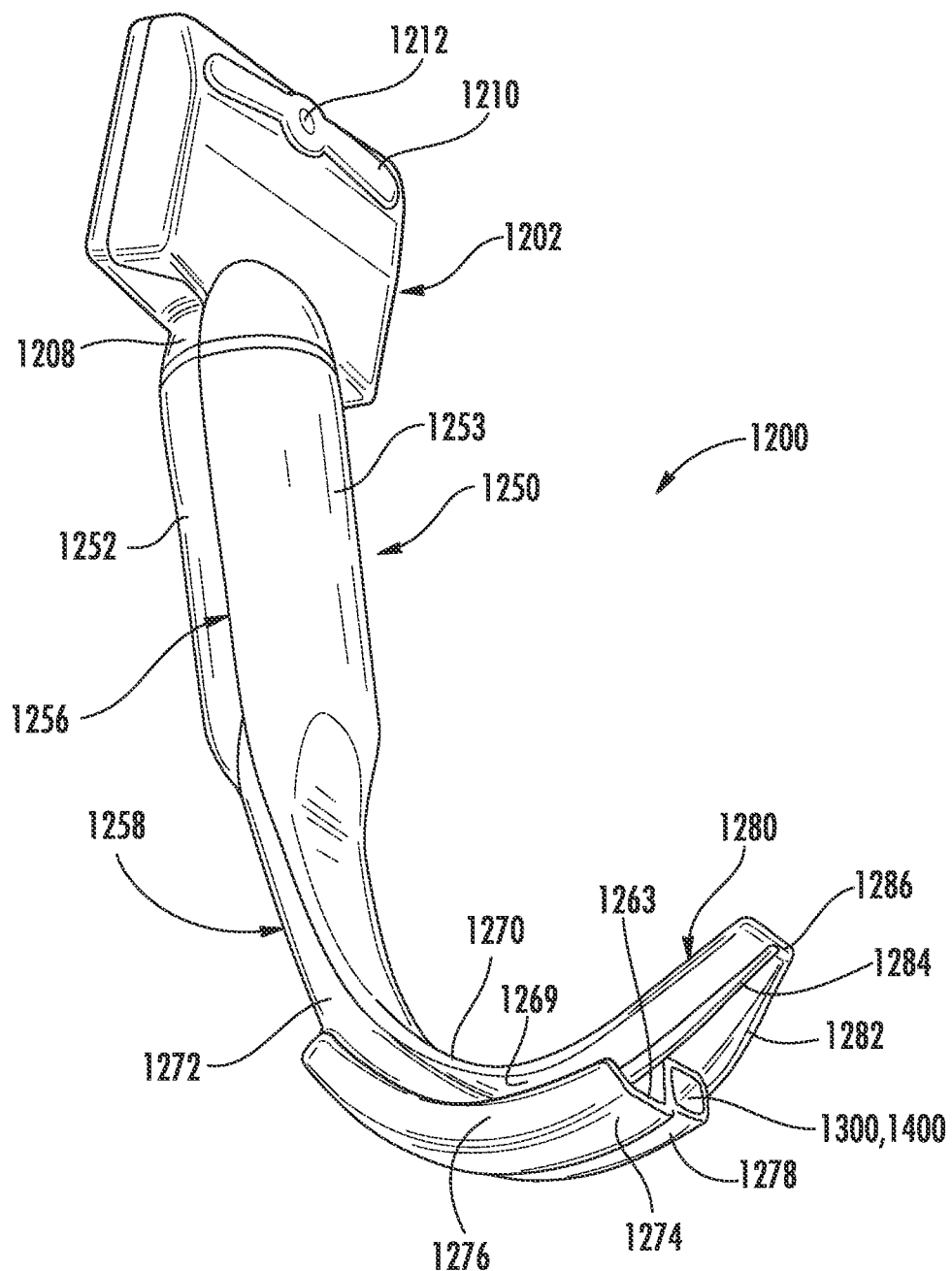

A further embodiment of a visualization instrument is illustrated in FIGS. 34 and 35. The medical visualization instrument is exemplified as a video laryngoscope 1200 comprising a first portion 1201 having a display device 1202, a housing 1370 (shown in FIGS. 49 and 50), and a support portion 1208 coupling display device 1202 to housing 1370. Video laryngoscope 1200 also comprises a blade 1250 having a handle 1256, which has a posterior side 1252 and an anterior side 1253 (shown in FIG. 35), and an insertable portion 1258. Although in use the handle will typically be in a primarily vertical orientation, in the context of the blade parts the terms anterior and posterior refer to one or the opposite sides of the blade. Display device 1202 includes a display screen 1204 surrounded by a frame 1205, and a video output port 1206. In one example, frame 1205 is metallized to dissipate static electricity. In another example, where display device 1202 is backlit, back lighting is disabled to save power until blade 1250 and first portion 1201 are connected. In a further example, display device 1202 is disabled entirely until blade 1250 and first portion 1201 are connected. In one example, a gasket is provided between connecting portions of blade 1250 and first portion 1201 to fluidly seal the connection.

Figure 39:
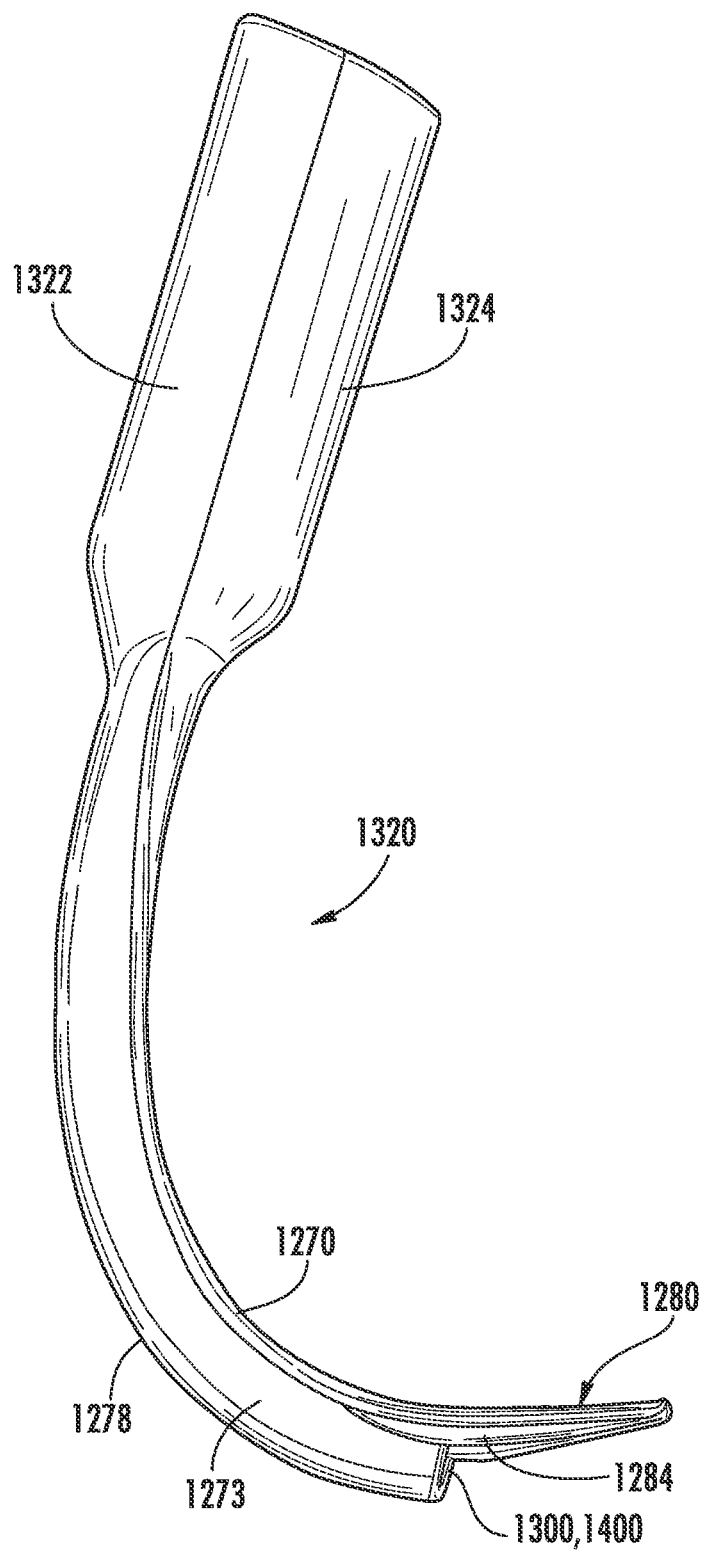
FIG. 39 is a lateral plan view of another embodiment of a blade of a visualization instrument.

Blade 1250 includes a plurality of guide walls forming a pathway for an endotracheal tube. The guide pathway is defined, at least in part, by an anterior guide surface and a medial guide surface. In one variation thereof, the anterior guide surface, e.g. anterior guide surface 1269, is substantially orthogonal to the medial guide surface e.g. the surface of medial wall 1272 shown in FIG. 35. Orthogonal guide surfaces are also shown in FIG. 39, illustrated by surfaces of anterior wall 1270 and medial wall 1273. In another variation thereof, shown in FIGS. 34 and 35, the guide pathway includes a proximal portion and a distal portion. The proximal portion of the guide pathway is defined by anterior guide surface 1269 and the surface of medial wall 1272 shown in FIG. 35. The distal portion of the guide pathway extends from the proximal portion and is further defined by posterior guide surface 1263 and the pathway facing surface of lateral guide wall 1276. An exemplary distal portion of a guide pathway is denoted by numeral 1262. In a further variation, the proximal portion of the guide pathway, measured along a center line of the insertion portion, is shorter than the distal portion. In another variation, the proximal portion length is at most 40% of a distal portion length.

In one example, the medial guide surface includes a transition portion extending through the proximal portion of the guide pathway and a longitudinally aligned portion extending through the distal portion of the guide pathway. In a variation thereof, the transition portion extends from a side of the insertable portion to the longitudinally aligned portion. In another variation thereof, exemplified in FIG. 34, the transition portion extends from a lateral side of the insertable portion to the longitudinally aligned portion. In a further variation thereof, the transition portion rotates from its proximal end to its distal end such that at its distal end it is orthogonal to the anterior guide surface.

Figure 36:
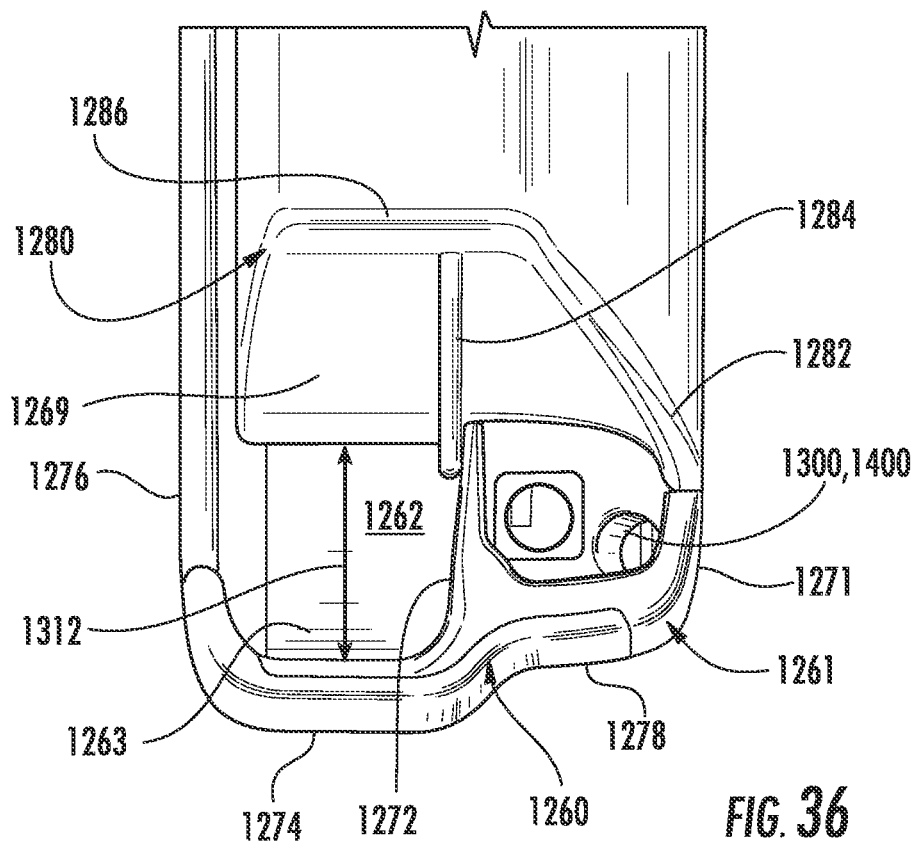
FIGS. 36 and 37 are partial distal and posterior views of the instrument of FIGS. 34 and 35.

Blade 1250 supports the imaging sensor and electronic components to electrically couple the imaging sensor to video display 1202. The imaging sensor may be electronically coupled wirelessly or by electrical conductors embedded in the insertable portion of the blade. In the exemplary embodiment shown in FIGS. 34-38, blade 1250 includes an electronics pathway defined by medial wall 1272, a posterior electronics pathway wall 1278, a lateral electronics pathway wall 1271, and anterior wall 1270. As best seen in FIG. 36, a distal cavity, denoted by numeral 1300, receives therein an imaging assembly 1400. A tip portion 1280 of blade 1250 extends distally beyond the electronics pathway. An imaging landmark, illustratively elongate protrusion 1284, may be provided in tip portion 1280 to assist the user in detecting the center of blade 1250 in the images viewed by the camera in imaging assembly 1400. An atraumatic tip, exemplified by ridge 1286, may also be provided. As shown in FIG. 35, tip portion 1280 may also include an atraumatic wall portion, illustratively wall portion 1282, which may also comprise any atraumatic wall portion as previously described. In additional examples, any of the blade embodiments described above and also with reference to FIGS. 10, 11, 34 and 39 are provided without any one or more of imaging landmarks, atraumatic tips, and atraumatic walls. In a further example, the blade supports an imaging assembly at its distal end and an electronic connector coupling the imaging assembly to the reusable portion is embedded within one of the walls of the insertable portion. For example, the electronic connector can comprise electrical conductors embedded in the medial wall of the blade. In a further example, the electronic connector is bonded to the insertable portion. For example, the connector may comprise a flat ribbon connector and may be bonded to the medial wall.

Resilient materials may be provided to add functionality to the blade. The exemplary embodiment described with reference to FIGS. 34-39, blade 1250 comprises two components comprising two materials. A first component 1261 comprises the first material and includes the handle and a rigid portion of the insertable portion of blade 1250. The first material imparts structure and rigidity to the blade. A second component 1260 comprises the second material and includes posterior guide wall 1274 and lateral guide wall 1276. The second material provides resiliency and softness relative to the first material. Second component 1260 is bonded to or over-molded onto first component 1261. Any known bonding method, such as adhesive, thermal, ultrasonic, and mechanical may be utilized to bond second component 1260 and first component 1261. In one example, the second material hardness is between 60 and 90 shore A. In a variation thereof, the second material hardness is between 75 and 85 shore A.

In yet another embodiment of a visualization instrument, alignment features are provided to facilitate engagement of the reusable portion and the handle. Exemplary mating alignment features were described with referring to FIG. 29. In a further example, the alignment features comprise mating alignment features which prevent engagement of the reusable portion and the blade unless the reusable portion is properly aligned with the blade. Advantageously, mating alignment features facilitate tactile engagement of the reusable portion and the blade without requiring a user to visually align the two components. A further example of mating alignment features is shown in FIG. 34 comprising a protrusion 1214 extending distally from support portion 1208 and engaging an opening in handle 1256, exemplified by a semi-circular opening 1254, to compel proper orientation of housing 1370 relative to handle 1256. In another example, the locations of the protrusion and the opening are reversed. In yet a further example, the opening comprises internal or external surface indentations, slots, or any other surface modification provided to engage protrusions and thereby indicate proper orientation of first portion 1201 relative to handle 1256. A further exemplary embodiment of mating alignment features is described below with reference to FIGS. 43 and 44. Alignment features may also comprise visual indications such as surface markings. In one example, surface markings comprise orientation or alignment indicia such as lines on the surface of the handle and the reusable portion. In another example, surface markings comprise anterior and posterior colors wherein the reusable portion and the handle exhibit one color on the anterior side and a different color on the posterior side.

Figure 38:
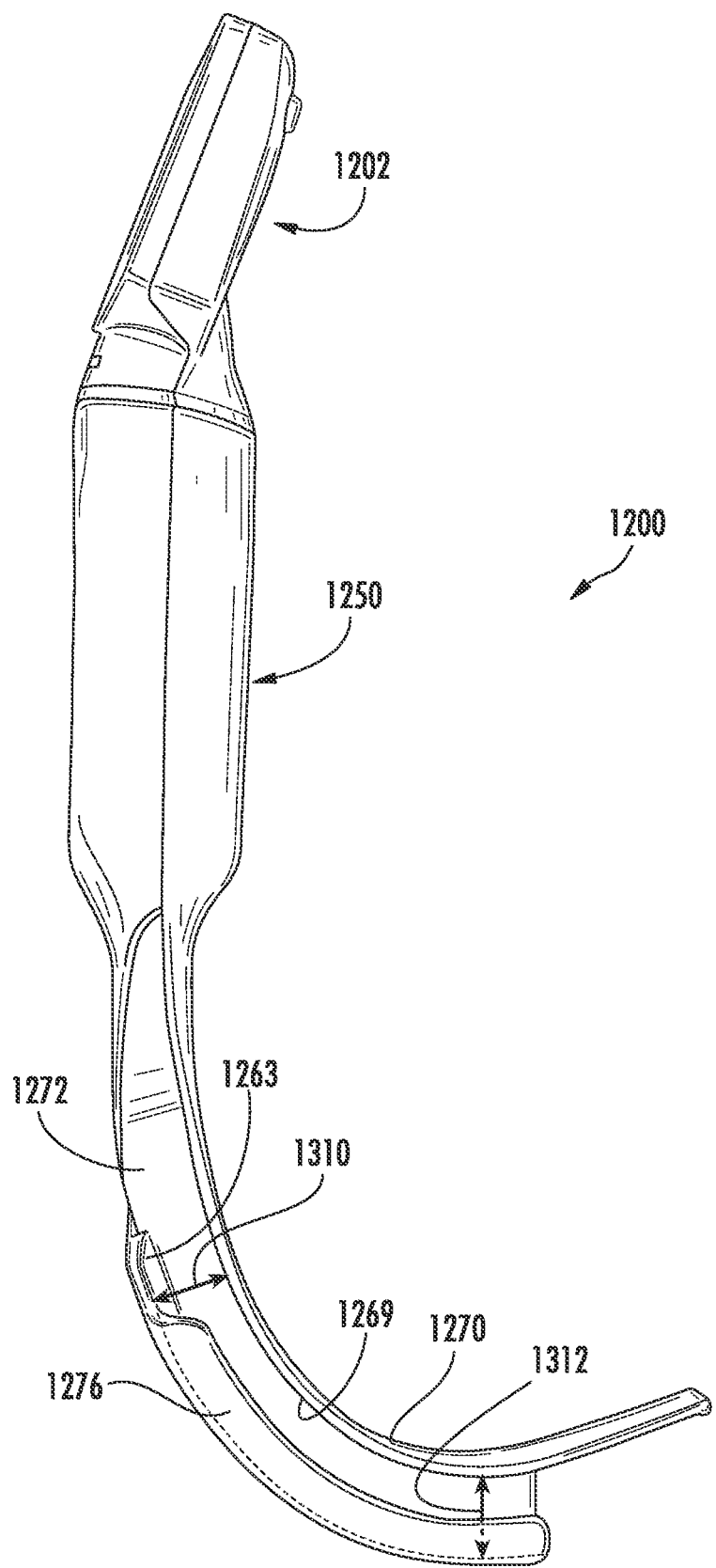
FIG. 38 is a lateral plan view of the instrument of FIGS. 34 and 35.

In another embodiment of the medical visualization instrument, guide pathway biasing features are provided to facilitate use of multiple endotracheal tube sizes. Generally, the biasing features exert anteriorly directed force on an endotracheal tube as it translates through the guide pathway. As shown in FIGS. 35, 36 and 38, insertable portion 1258 comprises an anterior guide surface 1269 of anterior wall 1270 and a posterior guide surface 1263 of posterior wall 1274 which define an anterior/posterior height. A proximal anterior/posterior height is denoted by numeral 1310 in FIG. 38 where a distal anterior/posterior height is denoted by numeral 1312. In one example, the proximal and distal anterior/posterior heights are substantially the same. In another variation, the posterior guide wall and the lateral guide wall are formed of a resilient material adapted to increase the distal anterior/posterior height when an endotracheal tube having sufficiently large diameter forces the posterior guide wall, which in its rest position defines an anterior/posterior height which is smaller than the diameter of the endotracheal tube, to move posteriorly away from the anterior wall. When the endotracheal tube is removed, the resilient posterior guide wall may return to its rest position. As shown in FIG. 34, component 1260 comprises the resilient material. In another example, a resilient bar or ramp protrudes from the posterior guide surface towards the guide pathway to provide the biasing force. Advantageously, a blade having a distal and biasing force as described herein permits use of one blade with any of a plurality of endotracheal tubes having different diameters as the biasing force ensures that, regardless of the diameter, the endotracheal tubes are biased towards the anterior wall as they exit the guide pathway and are thereby directed towards the vocal cords and visible by the camera.

In another embodiment of the disclosure, a visualization instrument is provided. The visualization instrument comprises a reusable portion, a handle portion, an insertable portion, and an imaging assembly. The insertable portion comprises a distal cavity at a distal end thereof and a connector accessible through the distal cavity to electrically and detachably couple the imaging assembly to the insertable portion. In one example thereof, the handle portion and the insertable portion are integrally coupled. In another example thereof, the imaging assembly is connected to the connector prior to use and subsequently disconnected. The insertable portion is then discarded while the imaging assembly may be cleaned and re-used. Advantageously, a reusable imaging assembly reduces the cost of the insertable portion which may be discarded after a single or a limited number of uses.

Figure 37:
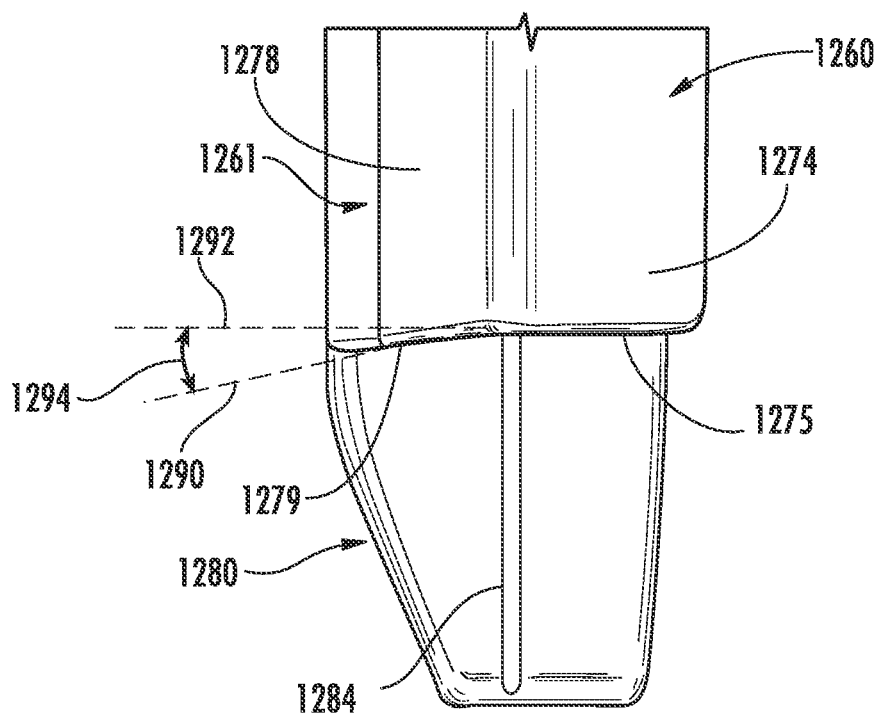

In another embodiment of the visualization instrument, image alignment features are provided to facilitate visualization of the endotracheal tube. An example of image alignment features is shown in FIG. 37 where posterior guide wall 1274 has a distal edge 1275 disposed substantially perpendicular to the longitudinal axis of blade 1250 and posterior electrical pathway wall 1278 has a distal edge 1279 disposed at an angle, defined by axial lines 1290 and 1292 and denoted by numeral 1294, relative to distal edge 1275. Imaging assembly 1400 may be aligned perpendicularly to axial line 1290 to angle the line of sight of imaging assembly 1400 as described above with reference to FIG. 4 to facilitate viewing the displacement of the endotracheal tube towards the vocal cords.

In another embodiment of the visualization instrument, a blade without posterior and lateral guide walls is provided. An example of such a blade is shown in FIG. 39 where a lateral view of a blade 1320 is illustrated. Anterior and posterior sides of blade 1320 are denoted by numerals 1324 and 1322. A medial wall is denoted by numeral 1273. Medial wall 1273 is substantially the same as medial wall 1272 except that it is shorter as medial wall 1273 does not extend to support posterior wall 1274. Some surgeons may prefer the additional freedom to control the endotracheal tube (without the lateral and posterior guide walls) provided by blade 1320 as compared to blade 1250.

In a further embodiment of the visualization instrument, rest features are provided which support the reusable portion when the reusable portion rests on a surface. The rest features comprise rest surfaces adapted to stabilize the medical instrument in a rest position. In one example, the rest surface has a coefficient of friction higher than the coefficient of friction of the distal surface of the display device. In one variation of the previous example, the rest surface comprises rubber. In another variation, the rest surface comprises a polymeric material with a coefficient of friction that is higher than the coefficient of friction of the material from which the display device frame is made. In another example, a rest surface extends from the distal surface of the display device. In one variation thereof, a rest surface is parallel to the supporting surface when the reusable portion is decoupled from the handle. In another variation thereof, a rest surface is parallel to the supporting surface when the reusable portion is coupled to the handle. In a further variation thereof, the display device comprises a rest feature having two rest surfaces. One rest surface supports the display device when the handle is coupled to the reusable portion and the other rest surface supports the display device when the handle is not coupled the reusable portion. In a further example, a switch cover is disposed between the rest surface and the screen and the rest surface prevents accidental activation of the switch. An example of a rest surface and switch cover will now be described with reference to FIGS. 35, 40 and 41 where, on its distal side, display device 1202 comprises a rest surface, illustratively rest bar 1210. Rest bar 1210 comprises a material having a coefficient of friction suitable for substantially preventing sliding of the reusable portion on the supporting surface. Exemplary materials include rubber and elastomeric polymers. In another example, the surface of the rest bar is textured to increase friction. For example, texture may comprise lines and bumps. A switch cover, illustratively cover 1212, sealingly covers an electrical switch, illustratively switch 1330 (shown in FIG. 41). Exemplary switches include push-button switches and toggle switches. Switch 1330 may be configured to turn power to the medical visualization instrument on and off. Advantageously, placing a power switch on the distal side of display device 1202 instead of the proximal side permits utilization of a larger portion of the proximal area of display device 1202 for display screen 1204 while providing an ergonomically attractive switch location. Rest bar 1210 is sufficiently thick to prevent accidental actuation of switch 1330 when rest bar 1210 supports display device 1202. In another example, the reusable portion has a rest surface on the distal side of display device 1202, without a rest bar, and the cover is recessed so as to prevent accidental activation of switch 1330. FIG. 40 also shows housing 1370 extending from support portion 1208 which connects housing 1370 and display device 1202.

In yet a further embodiment of the visualization instrument, external communication features are provided. Referring now to FIG. 42, in one example the display device 1202 includes a receptacle 1332 connected internally to electronic circuits configured to provide an image output. The image output may be a serial or parallel signal, and may a digital or analog signal. A connector 1334 extends from a cable 1336. Connector 1334 electronically couples receptacle 1332 to transfer the image output through cable 1336 to a remote device such as a computer, video monitor, or hardware interface configured to further transfer the image output for eventual display at a remote device. In the present example, display device 1202 comprises a cavity sealingly receiving a sealing portion disposed between connector 1334 and cable 1336, illustratively cavity 1333 and sealing portion 1338. Sealing portion 1338 and cavity 1333 are rectangularly shaped. In a variation of the previous example, the sealing portion and the cavity comprise another shape. Exemplary shapes include oval, circular, and square. Advantageously, sealing the connector and the receptacle prevents exposure of cavity 1333 to debris and contaminants and, as a result, display device 1202 may be more easily cleaned or disinfected. A similarly shaped cover without a cable is provided to seal cavity 1333 when it is not desired to provide an image output to a remote device.

Referring now to FIGS. 43 and 44, another example of an alignment feature is shown therein. As described above, the reusable portion comprises a housing insertable into the handle of the medical instrument. FIG. 43 illustrates an exemplary housing, denoted by numeral 1370, having a particular cross-sectional profile designed to easily mate with a corresponding cross-sectional profile of a handle. As shown, housing 1370 has a body 1372 with a generally oval cross-section and comprises an elongate protrusion, illustratively protrusion 1374, extending from the generally oval body 1372 in the longitudinal direction. As shown in FIG. 44, handle 1256 comprises two longitudinally disposed surfaces, embodied in ridges 1360, which together define a slot 1362 configured to receive protrusion 1374. In a variation of the previous example, the longitudinally disposed surfaces are formed by protrusions extending from the internal surface of the handle without forming ridges. For example, slot 1362 may be formed directly on the wall of the handle.

Figure 45:
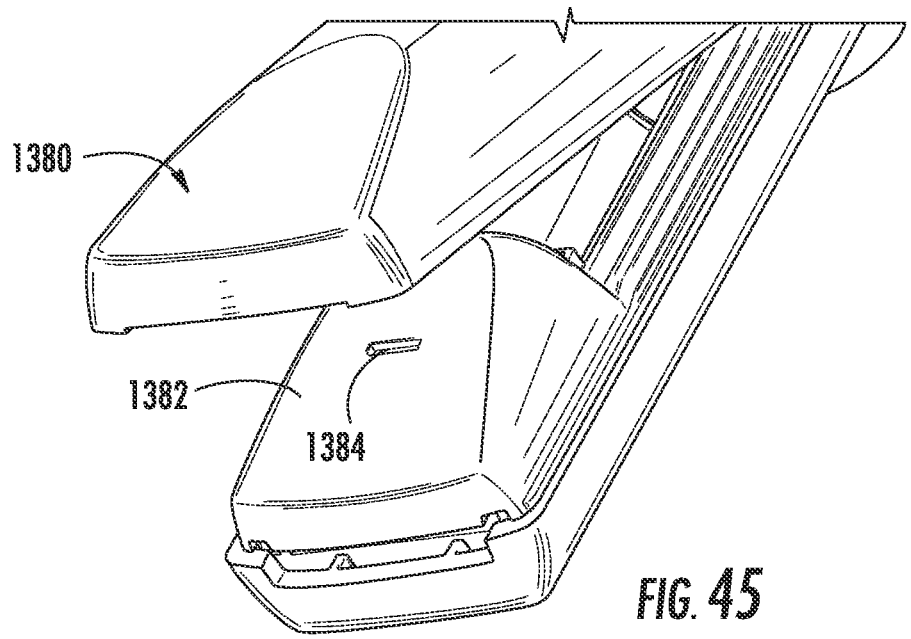
Figure 46:
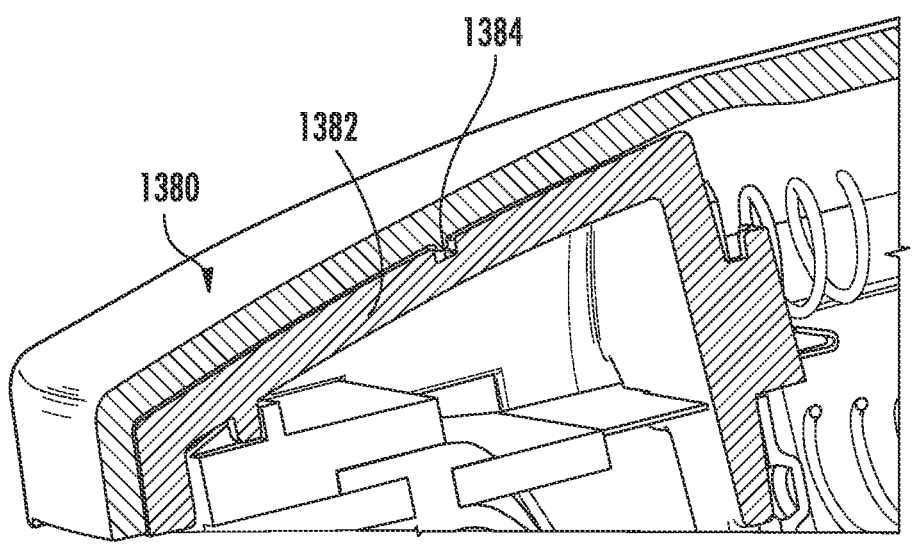

Referring now to FIGS. 45 and 46, a housing of a reusable portion is shown therein comprising a battery connection portion 1382 and a battery cover 1380. The housing also comprises a battery cover locking feature. In one example, the locking feature comprises a ridge and a slot. When battery cover 1380 is pressed against battery connection portion 1382 and a longitudinally oriented force is applied, the ridge and the slot mate. In one variation of the previous example, shown in FIG. 46 in a mated position, battery cover 1380 comprises a ridge and battery connection portion 1382 comprises a slot 1384. In another variation thereof, the positions of the slot and the ridge are reversed. In a further variation thereof, the slot and the ridge are located in lateral surfaces of battery connection portion 1382 and battery cover 1380.

FIGS. 47 and 48 are perspective and exploded views of an exemplary embodiment of an imaging assembly, illustratively imaging assembly 1400. Imaging assembly 1400 comprises a distal cover 1402, a camera holder 1404 having an imaging opening 1406 and an illumination opening 1408, a distal lens 1422, a camera barrel 1420, lenses 1424 and 1426, a gasket 1430, a camera 1432, a support board 1434 supporting camera 1432, a cable 1436, and a backing plate 1442 having a pressure component 1444 and a plurality of locking components 1446. Backing plate 1442 presses support board 1434 and lenses 1424 and 1426 in camera barrel 1420. Camera barrel 1420 is press-fit into an opening of camera holder 1404 to hold distal lens 1422 inside camera holder 1404. Gasket 1430 is optional and may be removed. If used, gasket 1430 seals imaging sensor 1432 inside camera barrel 1420 and prevents light from entering camera barrel 1420 and degrading the images. LED 1440 is coupled to camera holder 1404 to illuminate the space before distal cover 1402 through illumination opening 1408. In one variation of the previous example, distal cover 1402 is adhesively bonded to camera holder 1404 using a silicone release application method. Adhesive is provided on a silicone paper. The silicon paper and adhesive are applied to distal cover 1402. The silicone paper is then removed, and the newly exposed side of the adhesive is pressed against camera holder 1404 to secure distal cover 1402 thereto. Advantageously, the silicone release method described herein protects distal lens 1422 from inadvertent spearing of adhesive on its distal surface. The combination of a support housing and an imaging barrel simplifies assembly of the imaging assembly. In a variation of the example described above, only two lenses are used. In another variation thereof, the camera barrel and the camera holder are formed by single-mold inserts which cause the distal lens and second lens to self-align relative to the optical axis of the imaging assembly which simplifies the assembly process and reduces cost by eliminating the need for focusing features. In yet another variation thereof, the imaging assembly comprises a distal lens having a negative meniscus, and a doublet comprised of biconvex and negative meniscus elements. The distal and doublet lenses have aspheric surfaces which, combined with the meniscus and biconvex elements, achieve nearly diffraction limited performance.

Examples of visualization instruments comprising a reusable portion and a handle coupled to an insertable portion in a single piece construction were described above. In a further example of a visualization instrument, the insertable portion and the handle are detachably coupled. Any of the alignment and state features described above with reference to coupling of the handle and the reusable portion may also be applied to coupling of the handle and the insertable portion. In one example, the handle is integrally formed with the housing supporting the video display, and the insertable portion is detachably coupled to the handle. In one variation thereof, the insertable portion comprises walls defining a guide pathway. In another variation thereof, the insertable portion comprises an elongate tubular member.

While the invention has been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this invention pertains.

The invention claimed is:
1. A visualization instrument comprising:
a reusable portion including a display device, a processing device, and an energy source housing adapted to receive a self-contained energy source configured to power the display device and the processing device;
a camera including an imaging sensor, the camera outputting an image stream corresponding to a plurality of views obtained through the lens and electronically coupled to the display device to present images corresponding to the plurality of views with the display device;
an integrally formed single-piece blade including a handle portion and an insertable portion adjacent the handle portion, the handle portion including a proximal cavity configured to detachably receive the energy source housing and to support the display device and the processing device when the energy source housing is received in the proximal cavity, the blade thus detachably coupled to the reusable portion, the insertable portion insertable into a patient; and a camera identifier, a data storage device, and a plurality of camera identifiers stored in the data storage device, wherein the processing device compares the camera identifier to the plurality of camera identifiers to find a match and disables presentation of the images if the match is not found.

2. A visualization instrument as in claim 1, the visualization instrument further comprising:

a use indicia; and a sensing device electronically coupled to the processing device and sensing the use indicia, the processing device cooperating with the use indicia to determine a number of uses of the blade and to disable presentation of the images after the insertable portion has been used a permitted number of uses.

3. The visualization instrument of claim 2, wherein the permitted number of uses is one.

4. A visualization instrument as in claim 1, further comprising:

a sensing device electronically coupled to the processing device and sensing environmental variables including at least one of temperature and humidity, wherein the visualization instrument is operable to track a number of uses of the blade based on status changes of the environmental variables, each status change comprising an environmental variable exceeding a threshold for a predetermined amount of time.

5. The visualization instrument of claim 2, wherein the use indicia comprises a single-use fuse.

6. The visualization instrument of claim 2, further comprising an image sensor identifier, wherein the processing device determines the number of uses based on the image sensor identifier.

7. The visualization instrument of claim 6, wherein the image sensor identifier is stored in the camera.

8. The visualization instrument of claim 6, further comprising an electronic device storing the image sensor identifier, the electronic device supported by one of the handle portion and the insertable portion and electronically coupled to the processing device when the insertable portion is coupled to the display device.

9. The visualization instrument of claim 1, wherein the visualization instrument is adapted to intubate a patient with a tube, wherein the tube is distinguishable in the images presented with the display device as the tube passes through a field of view of the lens.

10. The visualization instrument of claim 1, wherein the visualization instrument is adapted to intubate the patient with a tube, the blade further comprising at least two guide surfaces defining a guide pathway having an open side configured to enable removal of the tube.

11. A visualization instrument as in claim 1, the visualization instrument further comprising:

tracking means for disabling presentation of the corresponding images after the insertable portion has been used a permitted number of uses, wherein the tracking means comprises a sensing device and a use indicia, the sensing device sensing the use indicia to determine a number of uses of the blade, the processing device cooperating with the tracking means to determine if the insertable portion has been used more than the permitted number of uses.

12. The visualization instrument of claim 11, wherein the tracking means comprises a single-use fuse.

13. The visualization instrument of claim 11, wherein the permitted number of uses is one.

14. The visualization instrument of claim 11, wherein the tracking means is operable to track when the insertable portion is used by evaluating environmental variables including at least one of temperature and humidity.

15. The visualization instrument of claim 11, wherein the tracking means comprises an identification feature configured to track the number of uses.

16. The visualization instrument of claim 15, wherein the identification feature is a camera identifier.

17. The visualization instrument of claim 2, wherein the use indicia comprises an identification feature detectable in the image stream.

18. The visualization instrument of claim 1, further comprising an identification component, wherein the processing device determines the number of uses based on the identification component.

19. The visualization instrument of claim 18, wherein the identification component is a unique feature detectable in the image stream.

20. The visualization instrument of claim 18, wherein the identification component is an electronic identifier.

21. The visualization instrument of claim 20, wherein the electronic identifier is a programmable identifier located in an integrated circuit in the insertable portion.

22. The visualization instrument of claim 18, wherein the identification component is a physical mark in the insertable portion.

23. The visualization instrument of claim 11, wherein the tracking means comprises an identification component, and the processing device is configured to determine a number of uses based on the identification component.

24. The visualization instrument of claim 23, wherein the identification component is a unique feature detectable in the image stream.

25. The visualization instrument of claim 23, wherein the identification component is an electronic identifier.

26. The visualization instrument of claim 25, wherein the electronic identifier is a programmable identifier located in an integrated circuit in the insertable portion.

27. The visualization instrument of claim 23, wherein the identification component is a physical mark in the insertable portion.

* * * * *